US012674200B2

(12) United States Patent
Engelthaler et al.

(10) Patent No.: US 12,674,200 B2
(45) Date of Patent: *Jul. 7, 2026

(54) METHODS AND KITS FOR THE DETECTION OF SARS-COV-2

(71) Applicant: THE TRANSLATIONAL GENOMICS RESEARCH INSTITUTE, Phoenix, AZ (US)

(72) Inventors: David Engelthaler, Flagstaff, AZ (US); Jolene Bowers, Flagstaff, AZ (US); James Schupp, Flagstaff, AZ (US)

(73) Assignee: THE TRANSLATIONAL GENOMICS RESEARCH INSTITUTE, Phoenix, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/931,893

(22) Filed: Sep. 13, 2022

(65) Prior Publication Data

US 2023/0043710 A1 Feb. 9, 2023

Related U.S. Application Data

(63) Continuation of application No. PCT/US2021/022114, filed on Mar. 12, 2021.

(60) Provisional application No. 62/989,550, filed on Mar. 13, 2020.

(51) Int. Cl.
*C12Q 1/6874* (2018.01)
*C12Q 1/682* (2018.01)
*C12Q 1/686* (2018.01)

(52) U.S. Cl.
CPC .......... *C12Q 1/6874* (2013.01); *C12Q 1/682* (2013.01); *C12Q 1/686* (2013.01)

(58) Field of Classification Search
CPC .......... C12N 2770/20022; C12Q 1/682; C12Q 1/686; C12Q 1/6874; C12Q 1/701
See application file for complete search history.

(56) References Cited

U.S. PATENT DOCUMENTS

| | | | |
|---|---|---|---|
| 11,214,843 B2 * | 1/2022 | Li | ........................ C12Q 1/701 |
| 2012/0107796 A1 | 5/2012 | Keim | |
| 2016/0319361 A1 | 11/2016 | Spetzler et al. | |
| 2016/0326572 A1 * | 11/2016 | Schupp | .................. C12Q 1/686 |
| 2019/0030187 A1 | 1/2019 | Lu | |
| 2020/0048722 A1 | 2/2020 | Nyan | |
| 2023/0128191 A1 | 4/2023 | Engelthaler | |

OTHER PUBLICATIONS

Shen et al. (Journal of Pharmaceutical Analysis, 2020, 10:97e101) (Year: 2020).*
Hadjinicolaou et al. (Arch. Virol., 2011, 156:671-680) (Year: 2011).*
Buck et al. (BioTechniques, 1999, 27:528-536) (Year: 1999).*
Lowe et al. (Nucleic Acids Research, 1990, vol. 18, No. 7, p. 1757-1761) (Year: 1990).*
Buck et al. (Biotechniques, 1999, 27(3):528-536) (Year: 1999).*
Corman et al., "Detection of 2019 novel coronavirus (2019-nCOV) by real-time RT-PCR", Euro Surveill., 25(3):1-8 (Jan. 23, 2020).
GenBank submission CX695252.1, ydd91d10.y2 Sea urchin EST Lib1 Strongylocentrotus purpuratus cDNA clone ydd91d10 5', mRNA sequence, Dec. 21, 2010 [online]. [Retrieved on Jul. 3, 2021]. Retrieved from the internet: <URL: https://www.ncbi.nlm.nih.gov/nuccore/CX695252>.
GenBank submission EH727004.1, CNMM13439.b1_N24.ab1 CNM(LMS) spotted knapweed Centaurea maculosa cDNA clone CNMM13439, mRNA sequence., Nov. 28, 2007, [online]. [Retrieved on Jul. 3, 2021]. Retrieved from the internet: <URL: https://www.ncbi.ntm.nih.gov/nuccore/EH727004>.
Xi Ng et al., "Precautions are Needed for COVID-19 Patients with Coinfection of Common Respiratory Pathogens", medRxiv preprint, (Mar. 5, 2020), URL: https://doi.org/10.1101/2020.02.29.20027698, (Jul. 3, 2021), XP055854576.
Xing et al., Post-discharge surveillance and positive virus detection in two medical staff recovered from coronavirus disease 2019 (COVID-19), China, Jan. to Feb. 2020. Euro Surveill. 2020;25(10).

* cited by examiner

*Primary Examiner* — Jeremy C Flinders
(74) *Attorney, Agent, or Firm* — FULLER IP LAW LLC; Rodney J. Fuller

(57) ABSTRACT

Methods, kits, and oligonucleotides used in the detection of the coronavirus strain, severe acute respiratory syndrome coronavirus 2 (SARS-CoV-2), are disclosed. In some aspects, the oligonucleotides are primers or probes used in the described methods or kits. The oligonucleotide consists of 40 or less nucleotides and has a nucleotide sequence that consists essentially of, or is a variant of, the nucleotide sequence of: SEQ ID NO:1, SEQ ID NO:2, SEQ ID NO:3, SEQ ID NO:5, SEQ ID NO:6, or SEQ ID NO:7. In some embodiments, the oligonucleotide is modified with an internal spacer or a detectable label. For example, the 5' terminus is labeled with a fluorophore and the 3' terminus is complexed to a quencher of fluorescence of said fluorophore. In some embodiments, the nucleotide sequence of the oligonucleotide further comprises a universal tail sequence.

5 Claims, 10 Drawing Sheets

Specification includes a Sequence Listing.

METHODS AND KITS FOR THE DETECTION OF SARS-COV-2

CROSS REFERENCE TO RELATED APPLICATIONS

The present application is a continuation of International Application No. PCT/US2021/022114, filed Mar. 12, 2021, which claims the benefit of U.S. provisional patent application No. 62/989,550, filed Mar. 13, 2020 titled "Methods and Kits for the Detection of SARS-CoV-2,", the contents of each of which are hereby incorporated by reference in their entireties.

INCORPORATION-BY-REFERENCE OF MATERIAL ELECTRONICALLY FILED

The official copy of the sequence listing is submitted electronically in ST.26 XML format having the file name "91482-245USCONseqList.xml" created on Sep. 13, 2022, and having a size of 17.632 bytes, and is filed concurrently with the specification. The Sequence Listing ST.26 XML file is part of the specification and is herein incorporated by reference in its entirety.

TECHNICAL FIELD

The present invention relates to the field of detection of coronavirus, and more particularly, severe acute respiratory syndrome coronavirus 2 (SARS-CoV-2), which has been implicated in the pathogenesis of the disease COVID-19.

BACKGROUND

The world is experiencing a global outbreak of coronavirus disease COVID-19 caused by SARS-CoV-2, which was first reported in China in December 2019. Symptoms of COVID-19 is flu-like symptoms and can lead to pneumonia or more severe conditions. However, most people infected with the COVID-19 virus and develop symptoms will experience only mild to moderate respiratory illness and recover without requiring special treatment. Older people, and those with underlying medical problems like cardiovascular disease, diabetes, chronic respiratory disease, and cancer are more likely to develop serious illness. More than a year after the first reported case of COVID-19, there still remains no specific treatment for COVID-19.

Unlike most other respiratory disease, COVID-19 is known to spread even from an asymptomatic infected person to a close contact. An estimated 40% of individuals with SARS-CoV-2 infection are asymptomatic. Accordingly, SARS-CoV-2 can easily quietly spread within the community. Identifying where SARS-CoV-2 infections are taking place in the community is key to slowing the spread of COVID-19. Unfortunately, limitations in identifying the infection resulted in COVID-19 being declared a pandemic by the World Health Organization. To date, the pandemic has yet to end, and SARS-CoV-2 continues to place public health and economic stresses on the world. Identification of the etiology of COVID-19 and related illnesses is important in order to understand risk factors, target surveillance, properly treat diagnosed COVID-19 patients, and to help limit additional outbreaks. Thus, detecting SARS-CoV-2 infection as early and as fast as possible with a sensitive, reliable test remains crucial for ending the COVID-19 pandemic.

SUMMARY

A need exists for a rapid molecular assay to diagnose patients with suspected SARS-CoV-2, to aid in COVID-19 diagnosis, and for future surveillance and epidemiology. The emergence and rapid spread of SARS-CoV-2 to numerous areas throughout the world, has necessitated preparedness and response in public health laboratories, as well as health care and other areas of society in general. The availability of specific and sensitive assays for the detection of the virus are essential for accurate diagnosis of cases, assessment of the extent of the outbreak, monitoring of intervention strategies and surveillance studies. The disclosed oligonucleotides, methods, and kits can be used in an assay to detect the presence or absence of SARS-CoV-2 virus in a biological sample and to aid in diagnosis of a subject as having COVID-19 disease, thereby informing treatment decisions for the subject. The disclosed assays target specific nucleic acid sequences from the genome of the SARS-CoV-2 virus, in particular, regions in the nucleocapsid protein (N protein) gene and spike protein (S protein) gene of SARS-CoV-2. By targeting one or more regions of the SARS-CoV-2 virus RNA, the assays differentiate SARS-CoV-2 from other clinically relevant non-SARS-CoV-2 coronaviruses.

Accordingly, in some aspects, the disclosure relates to oligonucleotides (having a 5' terminus and a 3' terminus) that recognize regions in the N protein gene or the S protein gene of SARS-CoV-2. The nucleotide sequence of the oligonucleotide consists of 40 or less nucleotides and has a nucleotide sequence that consists essentially of, or is a variant of, the nucleotide sequence of: SEQ ID NO:1, SEQ ID NO:2, SEQ ID NO:3, SEQ ID NO:5, SEQ ID NO:6, or SEQ ID NO:7. In some aspects, the variant thereof has no more than 5 substitutions, deletions, or additions. In some embodiments, the oligonucleotide is modified with an internal spacer or a detectable label, for example, when the nucleotide sequence of the oligonucleotide comprises SEQ ID NO:3 or SEQ ID NO:7. In some embodiments, the 5' terminus is labeled with a fluorophore and the 3' terminus is complexed to a quencher of fluorescence of said fluorophore. In certain embodiments, the nucleotide sequence of the oligonucleotide further comprises a universal tail sequence, for example, a sequence selected from SEQ ID NO:13 and SEQ ID NO:14.

The kits described herein comprises a primer pair, wherein at least one primer of the primer pair consists of less than 40 nucleotides and has a nucleotide sequence that consists essentially of, or is a variant of, the nucleotide sequence of: SEQ ID NO:1, SEQ ID NO:2, SEQ ID NO:5, or SEQ ID NO:6, and wherein the primer pair is capable of detecting SARS-CoV-2, if present, in the sample by amplification; and SARS-CoV-2 detection reagents. In some aspects, the nucleotide sequence of the variant has no more than 5 substitutions, deletions, or additions when compared to the nucleotide sequence of SEQ ID NO:1, SEQ ID NO:2, SEQ ID NO:5, or SEQ ID NO:6. In some embodiments, the at least one of the primers of the primer pair is modified with an internal spacer or a detectable label. In certain embodiments, the kit further comprises a probe modified with an internal spacer or detectable label. The probe hybridizes to an oligonucleotide having a nucleotide sequence that consists essentially of SEQ ID NO:4 or SEQ ID NO:8. In some aspects, the probe is labeled with a fluorophore and a quencher of fluorescence of the fluorophore.

In particular embodiments of the kit, SEQ ID NO:1 and SEQ ID NO:2 make the primer pair. In other embodiments, SEQ ID NO:5 and SEQ ID NO:6 make the primer pair. In still other embodiments, the kit comprises two primer pairs, which are made of SEQ ID NO:1 and SEQ ID NO:2 for one pair and SEQ ID NO:5 and SEQ ID NO:6 for the other pair.

The kit may further comprise running buffer and a test strip. The test strip comprises filter paper and/or chitosan.

In particular embodiments, the kit comprises a first forward primer comprising SEQ ID NO: 1, a first reverse primer comprising SEQ ID NO: 2, a detectably labeled first probe comprising SEQ ID NO: 3, a second forward primer comprising SEQ ID NO: 5, a second reverse primer comprising SEQ ID NO: 6, a detectably labeled second probe comprising SEQ ID NO:7, and optionally one or more PCR reagents. The first forward primer, the first reverse primer, the detectably labeled first probe, the second forward primer, the second reverse primer, the detectably labeled second probe, and the one or more PCR reagents may be lyophilized. The kit may further comprise an indication of a result that signifies the presence of SARS-CoV-2 and an indication of a result that signifies the absence of SARS-CoV-2. The result may comprise a Ct value or a Cq value.

In certain embodiments, the kit comprises two primer pairs. The sequence of one primer of the first primer pair consists essentially of: SEQ ID NO:1, SEQ ID NO:1 and a universal tail sequence, or SEQ ID NO:9. The sequence of the other primer of the first primer pair consists essentially of: SEQ ID NO:2, SEQ ID NO:2 and a universal tail sequence, or SEQ ID NO:10. The sequence of one primer of the second primer pair consists essentially of: SEQ ID NO:5, SEQ ID NO:5 and a universal tail sequence, or SEQ ID NO:11. The sequence of the other primer of the second primer pair consists essentially of: SEQ ID NO:6, SEQ ID NO:6 and a universal tail sequence, or SEQ ID NO:12.

The methods described herein comprise mixing the biological sample in vitro with a primer pair that is capable of amplifying a SARS-CoV-2 amplicon product, if the SARS-CoV-2 polynucleotide is present in the biological sample, and amplifying the SARS-CoV-2 amplicon product. At least one primer of the primer pair consists of 40 or less nucleotides and has a nucleotide sequence that consists essentially of, or is a variant of, the nucleotide sequence of: SEQ ID NO:1, SEQ ID NO:2, SEQ ID NO:5, or SEQ ID NO:6. In some implementations, the nucleotide sequence of the variant has no more than 5 substitutions, deletions, or additions when compared to the nucleotide sequence of SEQ ID NO:1, SEQ ID NO:2, SEQ ID NO:5, or SEQ ID NO:6. In some implementations, the primer pair comprises a first primer pair that amplifies a N protein gene amplicon product of SARS-CoV-2 and a second primer pair that amplifies a S protein gene amplicon product of SARS-CoV-2. For example, the primer pair consists of: SEQ ID NO:1 and SEQ ID NO:2; or SEQ ID NO:5 and SEQ ID NO:6. In some implementations, the primer pair includes at least two primer pairs comprising SEQ ID NO:1 and SEQ ID NO:2; and SEQ ID NO:5 and SEQ ID NO:6. In some aspects, the amplicon product has a nucleotide sequence that consists essentially of SEQ ID NO:4 or SEQ ID NO:8.

The method further comprises contacting the SARS-CoV-2 amplicon product with a probe having a nucleotide sequence capable of hybridizing to the SARS-CoV-2 amplicon product, the probe being modified with an internal spacer or detectable label, and detecting whether SARS-CoV-2 polynucleotides are present in the biological sample by detecting the detectable label when the probe hybridizes to the SARS-CoV-2 amplicon. In particular implementations, the nucleotide sequence of the probe comprises the sequence of SEQ ID NO:3 or SEQ ID NO:7. In some aspects, the probe is labeled with a fluorophore and a quencher of fluorescence of the fluorophore. The nucleic acid amplification may comprise calculating a Ct value or a Cq value.

In some embodiments, the biological sample comprises a nasopharyngeal swab sample or sputum. In some aspects, the biological sample is from a human.

In particular embodiments of the methods, two primer pairs are mixed with the biological sample. The sequence of one primer of the first primer pair consists essentially of: SEQ ID NO:1, SEQ ID NO:1 and a universal tail sequence, or SEQ ID NO:9. The sequence of the other primer of the first primer pair consists essentially of: SEQ ID NO:2, SEQ ID NO:2 and a universal tail sequence, or SEQ ID NO:10. The sequence of one primer of the second primer pair consists essentially of: SEQ ID NO:5, SEQ ID NO:5 and a universal tail sequence, or SEQ ID NO:11. The sequence of the other primer of the second primer pair consists essentially of: SEQ ID NO:6, SEQ ID NO:6 and a universal tail sequence, or SEQ ID NO:12. Where the sequence of one primer of the first primer pair consists essentially of SEQ ID NO:9 or SEQ ID NO:1 and a universal tail sequence; the sequence of the other primer of the first primer pair consists essentially of SEQ ID NO:10 or SEQ ID NO:2 and a universal tail sequence; the sequence of one primer of the second primer pair consists essentially of SEQ ID NO:11 or SEQ ID NO:5 and a universal tail sequence; and the sequence of the other primer of the second primer pair consists essentially of SEQ ID NO:12 or SEQ ID NO:6 and a universal tail sequence, the method may further comprise analyzing the nucleic acid amplification products by sequencing the nucleic acid amplification products using next-generation sequencing. Accordingly, the method also further comprises adding an index to the nucleic acid amplification products using at least one indexing oligonucleotide. In some aspects, the at least one indexing oligonucleotide comprises a complementary sequence that recognizes the universal tail sequence, SEQ ID NO:13, or SEQ ID NO:14.

In some implementations, the method of detecting SARS-CoV-2 in a subject may include the steps of adding to a mixture containing a sample from the subject, (a) a first forward primer comprising SEQ ID NO: 1, (b) a first reverse primer comprising SEQ ID NO: 2, (c) a second forward primer comprising SEQ ID NO: 5, and (d) a second reverse primer comprising SEQ ID NO: 6, subjecting the mixture to conditions that allow nucleic acid amplification, and detecting the presence or absence of SARS-CoV-2 by analyzing the nucleic acid amplification products. In various embodiments, the method further comprises adding to the mixture a detectably labeled first probe comprising SEQ ID NO: 3 and a detectably labeled second probe comprising SEQ ID NO: 7, and detecting the detectably labeled first probe and the detectably labeled second probe, thereby detecting the presence of SARS-CoV-2 in the subject. In various embodiments, the first forward primer and the second forward primer may further include a first universal tail sequence comprising SEQ ID NO: 13, and wherein the first reverse primer and the second reverse primer include a second universal tail sequence comprising SEQ ID NO: 14. The method may further comprise adding an index to the nucleic acid amplification products using at least one indexing oligonucleotide. The method may further comprise analyzing the nucleic acid amplification products by sequencing the nucleic acid amplification products using next-generation sequencing.

The foregoing features and elements may be combined in various combinations without exclusivity, unless expressly indicated otherwise. These features and elements as well as the operation thereof will become more apparent in light of the following description. It should be understood, however, the following description is intended to be exemplary in nature and non-limiting.

DETAILED DESCRIPTION

Figure 1:
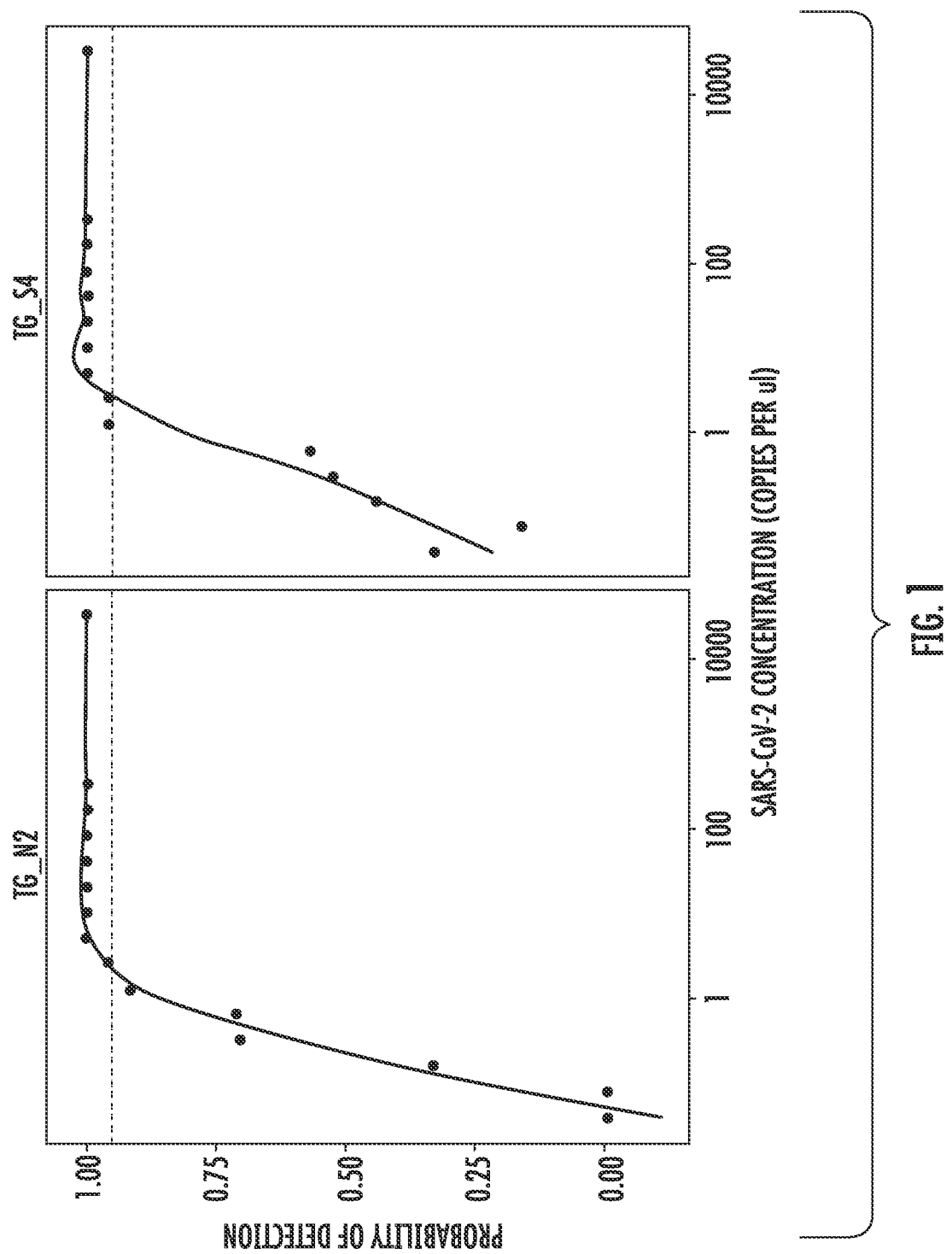
FIG. 1 depicts the probability of detection by SARS-CoV-2 concentration based on analytical sensitivity data.

It is to be understood that unless specifically stated otherwise, references to "a," "an," and/or "the" may include one or more than one and that reference to an item in the singular may also include the item in the plural. Reference to an element by the indefinite article "a," "an" and/or "the" does not exclude the possibility that more than one of the elements are present, unless the context clearly requires that there is one and only one of the elements. As used herein, the term "comprise," and conjugations or any other variation thereof, are used in its non-limiting sense to mean that items following the word are included, but items not specifically mentioned are not excluded.

The present invention relates to methods and kits for assaying for the presence of SARS-CoV-2 in a sample and to oligonucleotides, reagents and kits useful in such assays. The methods, kits, and oligonucleotides are specific and accurate for detecting SARS-CoV-2. The disclosed methods and assays detect SARS-CoV-2 RNA, in particular RNA encoding the nucleocapsid protein (N protein) or the spike protein (S protein).

As used herein, the term "sample" (or specimen) may refer to any source in which coronavirus nucleic acids may be detectable. A sample may be derived from anywhere that a virus may be found including soil, air, water, solid surfaces (whether natural or artificial,) culture media, foodstuffs, and any interfaces between or combinations of these elements. Thus, a sample may be an environmental sample or a biological sample, such as a sample obtained from a subject. As used herein, a biological sample includes cells, tissues, and bodily fluids, such as: blood; derivatives and fractions of blood, such as plasma or serum; biopsied or surgically removed tissue, including tissues that are, for example, unfixed, frozen, fixed in formalin and/or embedded in paraffin; tears; milk; skin scrapes; surface washings; urine; sputum; cerebrospinal fluid; prostate fluid; pus; bone marrow aspirates; lymph fluid; ascites; serous fluid; pleural effusion; semen; amniotic fluid; stool; or hair. Samples may be collected by any method now known or yet to be disclosed, including swiping or swabbing an area or orifice, removal of a piece of tissue as in a biopsy, or any method known to collect bodily fluids. In some aspects, a biological sample includes nasal swab, nasopharyngeal swab, bronchial wash, or bronchioalveolar lavage fluid (BALF) from a subject. As used herein, the term "subject" refers includes humans or animals. Emphasis must be placed on the timely collection and appropriate handling of patient samples in order to increase the likelihood of detection of RNA viruses, in this case SARS-CoV-2 detection.

As used herein, the method of or the assay, kit, or oligonucleotides for the detection of SARS-CoV-2 is "specific" for SARS-CoV-2 if the method or the assay using the kit or oligonucleotides can be conducted under conditions that permit the detection of SARS-CoV-2 without exhibiting cross-reactivity to human DNA, or to DNA (or cDNA) of other pathogens, especially other coronavirus pathogens. In particular, an assay for the detection of SARS-CoV-2 is specific for SARS-CoV-2 if it can be conducted under conditions that permit it to detect SARS-CoV-2 without exhibiting cross-reactivity to DNA (or cDNA) of other commonly known human respiratory pathogens or the diverse microbial population in a typical human respiratory tract. More preferably, the assay for the detection of SARS-CoV-2 is said to be specific for SARS-CoV-2 if it can be conducted under conditions that permit it to detect SARS-CoV-2 without exhibiting cross-reactivity to DNA (or cDNA) of SARS-CoV, MERS-CoV, human coronaviruses 229E, 0C43, HKU1, or NL63, adenovirus, human metapneumovirus, parainfluenza virus 1-4, Influenza A, Influenza B, enterovirus, respiratory syncytial virus (RSV), rhinovirus, *Chlamydophila pneumoniae, Haemophilus influenzae, Legionella pneumophila, Mycobacterium tuberculosis, Streptococcus pneumoniae, Streptococcus pyogenes, Bordetella pertussis, Mycoplasma pneumoniae, Pneumocystis jirovecii, Candida albicans, Pseudomonas aeruginosa, Staphylococcus epidermis, Staphylococcus salivarius,* or pooled human nasal fluid.

As used herein, an assay for the detection of SARS-CoV-2 is said to be "precise" or "accurate" for SARS-CoV-2 if the unknown sample contains ≥2590 copies of the SARS-CoV-2 viral genome (see paragraph 0106.)

The methods and assays described herein are for the detection of SARS-CoV-2 in a sample in vitro. The disclosed methods and assays include polymerase chain reaction (PCR) test for the detection of nucleic acid from the SARS-CoV-2 virus. In particular embodiments, the disclosed methods and assays include a real-time reverse transcription PCR (rRT-PCR) test for the qualitative detection of nucleic acid from the SARS-CoV-2 virus. The disclosed SARS-CoV-2 primer and probe sets are designed to detect RNA from the SARS-CoV-2 virus in biological samples from patients, such as patients suspected of having COVID-19.

In some implementations, the biological sample is pre-treated to extract RNA that may be present in the sample. Alternatively, the sample is evaluated without prior RNA extraction. For example, rRT-PCR assays of the present invention may be envisioned as involving multiple reaction steps:

(1) the reverse transcription of SARS-CoV-2 RNA that may be present in the clinical sample that is to be evaluated for SARS-CoV-2 presence;

(2) the PCR-mediated amplification of the SARS-CoV-2 cDNA produced from such reverse transcription;

(3) the hybridization of SARS-CoV-2-specific probes to such amplification products;

(4) the double-strand-dependent 5'→3' exonuclease cleavage of the hybridized SARS-CoV-2-specific probes; and (5) the detection of the unquenched probe fluorophores signifying that the evaluated clinical sample contained SARS-CoV-2.

It will be understood that such steps may be conducted separately (for example, in two or more reaction chambers, or with reagents for the different steps being added at differing times, etc.). However, it is preferred that such steps are to be conducted within the same reaction chamber, and that all reagents needed for the rRT-PCR assays of the present invention are to be provided to the reaction chamber at the start of the assay. It will also be understood that although the PCR is the preferred method of amplifying SARS-CoV-2 cDNA produced via reverse transcription, other DNA amplification technologies could alternatively be employed.

Accordingly, in a preferred embodiment, the rRT-PCR assays of the present invention comprise incubating a clinical sample in the presence of a DNA polymerase, a reverse transcriptase, one or more pairs of SARS-CoV-2-specific primers, one or more SARS-CoV-2-specific probes (typically, at least one probe for each region being amplified by an employed pair of primers), deoxynucleotide triphosphates (dNTPs) and buffers. The conditions of the incubation are cycled to permit the reverse transcription of SARS-CoV-2 RNA, the amplification of SARS-CoV-2 cDNA, the hybridization of SARS-CoV-2-specific probes to such cDNA, the cleavage of the hybridized SARS-CoV-2-specific probes and the detection of unquenched probe fluorophores.

The primer pair comprises a forward primer that hybridizes to a polynucleotide portion of a first strand of a DNA molecule and a reverse primer that hybridizes to a polynucleotide portion of a second (and complementary) strand of such DNA molecule. The forward and reverse primers will permit the amplification of a region of the N protein gene or a region of the S protein gene. The amplification of either of such targets alone is sufficient for the specific determination of SARS-CoV-2 presence in clinical samples. It is, however, preferred to assay for SARS-CoV-2 by amplifying both such targets for improved confidence in the assay results.

The presence of such amplified molecules is preferably detected using probes that are capable of hybridizing to an oligonucleotide region present within the oligonucleotide that is amplified by the above-described SARS-CoV-2-specific primers. Such detection can be accomplished using any suitable method, e.g., molecular beacon probes, scorpion primer-probes, TaqMan® probes, etc. All of these methods employ an oligonucleotide that is labeled with a fluorophore and complexed to a quencher of the fluorescence of that fluorophore.

A wide variety of fluorophores and quenchers are known and are commercially available and may be used in accordance with the methods of the present invention. Preferred fluorophores include the fluorophores Biosearch Blue, Alexa488, FAM, Oregon Green, Rhodamine Green-X, NBD-X, TET, Alexa430, BODIPY R6G-X, CAL Fluor Gold 540, JOE, Yakima Yellow, Alexa 532, VIC, HEX, and CAL Fluor Orange 560 (which have an excitation wavelength in the range of about 352-538 nm and an emission wavelength in the range of about 447-559 nm, and whose fluorescence can be quenched with the quencher BHQ1), or the fluorophores RBG, Alexa555, BODIPY 564/570, BODIPY TMR-X, Quasar 570, Cy3, Alexa 546, NED, TAMRA, Rhodamine Red-X, BODIPY 581/591, Redmond Red, CAL Fluor Red 590, Cy3.5, ROX, Alexa 568, CAL Fluor Red 610, BODIPY TR-X, Texas Red, CAL Fluor Red 635, Pulsar 650, Cy5, Quasar 670, CY5.5, Alexa 594, BODIPY 630/650-X, or Quasar 705 (which have an excitation wavelength in the range of about 524-690 nm and an emission wavelength in the range of about 557-705 nm, and whose fluorescence can be quenched with the quencher BHQ2). The preferred SARS-CoV-2-specific TaqMan probes of the present invention are labeled with either the fluorophore 2',7'-dimethoxy-4',5'-dichloro-6-carboxyfluorescein ("JOE") or the fluorophore 5(6)-carboxyfluorescein ("FAM") on their 5' termini. JOE is a xanthene fluorophore with an emission in yellow range (absorption wavelength of 520 nm; emission wavelength of 548 nm). FAM is a carboxyfluorescein molecule with an absorption wavelength of 495 nm and an emission wavelength of 517 nm; it is typically provided as a mixture of two isomers (5-FAM and 6-FAM). Quasar 670 is similar to cyanine dyes, and has an absorption wavelength of 647 nm and an emission wavelength of 670 nm.

The black hole quencher 1 ("BHQ1") is a preferred quencher for FAM and JOE fluorophores. BHQ1 quenches fluorescent signals of 480-580 nm and has an absorption maximum at 534 nm.

The black hole quencher 2 ("BHQ2") is a preferred quencher for Quasar 670. BHQ2 quenches fluorescent signals of 560-670 nm and has an absorption maximum at 579 nm.

JOE, FAM, Quasar 670, BHQ1 and BHQ2 are widely available commercially and are coupled to oligonucleotides using methods that are well known. Oligonucleotide probes of any desired sequence labeled may be obtained commercially already labeled with a desired fluorophore and complexed with a desired quencher.

As discussed above, the proximity of the quencher of a TaqMan® probe to the fluorophore of the probe results in a quenching of the fluorescent signal. Incubation of the probe in the presence of a double-strand-dependent 5'→3' exonuclease (such as the 5"→3" exonuclease activity of Taq polymerase) cleaves the probe when it has hybridized to a complementary target sequence, thus separating the fluorophore from the quencher and permitting the production of a detectable fluorescent signal.

Molecular beacon probes can alternatively be employed to detect amplified SARS-CoV-2 oligonucleotides in accordance with the present invention. Molecular beacon probes are also labeled with a fluorophore and complexed to a quencher. However, in such probes, the quenching of the fluorescence of the fluorophore only occurs when the quencher is directly adjacent to the fluorophore. Molecular beacon probes are thus designed to adopt a hairpin structure while free in solution (thus bringing the fluorescent dye and quencher into close proximity with one another). When a molecular beacon probe hybridizes to a target, the fluorophore is separated from the quencher, and the fluorescence of the fluorophore becomes detectable. Unlike TaqMan probes, molecular beacon probes are designed to remain intact during the amplification reaction, and must rebind to target in every cycle for signal measurement.

Scorpion primer-probes can alternatively be employed to detect amplified SARS-CoV-2 oligonucleotides in accordance with the present invention. Scorpion primer-probes are also designed to adopt a hairpin structure while free in solution and are also labeled with a fluorophore at their 5' terminus and complexed to a quencher at their 3' terminus. Scorpion primer-probes differ from molecular beacon probes in that their 3'-end is attached to their 5'-end by a hexathylene glycol (HEG) blocker. Such attachment prevents the polymerase-mediated extension of the 3' terminus of the scorpion primer-probe. However, after the scorpion primer-probe has bound to its target DNA, the polymerase copies the sequence of nucleotides from its 3'-end. In the next denaturation step, the specific sequence of the scorpion primer-probe binds to the complementary region within the same strand of newly amplified DNA. This hybridization opens the hairpin structure and, as a result, separates the molecules fluorophore from its quencher and permits fluorescence to be detected.

In a preferred embodiment, the probes of the present invention are TaqMa® probes. As described above, such probes are labeled on their 5' termini with a fluorophore and are complexed on their 3' termini with a quencher of the fluorescence of that fluorophore. In order to simultaneously detect the amplification of two polynucleotide portions of SARS-CoV-2, two TaqMan probes are employed that have different fluorophores (with differing and distinguishable emission wavelengths); the employed quenchers may be the same or different. In one embodiment of the invention, the 5' terminus of the first probe is labeled with the fluorophore JOE, and the 3' terminus of such probe is complexed to the quencher BHQ1 and the 5' terminus of the second probe is labeled with the fluorophore FAM, and the 3' terminus of such probe is complexed to the quencher BHQ1. In an alternative embodiment, the 5' terminus of the first probe is labeled with the fluorophore FAM, and the 5' terminus of the second probe is labeled with the fluorophore JOE. The use of such two fluorophores permits both probes to be used in the same assay.

The rRT-PCR assay described herein comprises one or more pairs of primers that amplify regions of the N protein and/or the S protein of SARS-CoV-2. In one embodiment, the assay comprises a first primer pair and probe targeting the nucleocapsid protein gene (N protein gene) of SARS-CoV-2 and a second primer pair and probe targeting the spike protein gene (S protein gene) of SARS-CoV-2. The methods of detecting SARS-CoV-2 in a sample in vitro comprise mixing the biological sample in vitro with a primer pair that is capable of amplifying a SARS-CoV-2 amplicon product, if the SARS-CoV-2 polynucleotide is present in the biological sample, and amplifying the SARS-CoV-2 amplicon product. At least one primer of the primer pair consists of 40 or less nucleotides and has a nucleotide sequence that consists essentially of, or is a variant of, the nucleotide sequence of: SEQ ID NO:1, SEQ ID NO:2, SEQ ID NO:5, or SEQ ID NO:6. In some implementations, the nucleotide sequence of the variant has no more than 5 substitutions, deletions, or additions when compared to the nucleotide sequence of SEQ ID NO:1, SEQ ID NO:2, SEQ ID NO:5, or SEQ ID NO:6. In some implementations, the primer pair comprises a first primer pair that amplifies a N protein gene amplicon product of SARS-CoV-2 and a second primer pair that amplifies a S protein gene amplicon product of SARS-CoV-2. For example, the primer pair consists of: SEQ ID NO:1 and SEQ ID NO:2; or SEQ ID NO:5 and SEQ ID NO:6. In some implementations, the primer pair includes at least two primer pairs comprising SEQ ID NO:1 and SEQ ID NO:2; and SEQ ID NO:5 and SEQ ID NO:6. In some aspects, the amplicon product has a nucleotide sequence that consists essentially of SEQ ID NO:4 or SEQ ID NO:8.

The method further comprises contacting the SARS-CoV-2 amplicon product with a probe having a nucleotide sequence capable of hybridizing to the SARS-CoV-2 amplicon product, the probe being modified with an internal spacer or detectable label, and detecting whether SARS-CoV-2 polynucleotides are present in the biological sample by detecting the detectable label when the probe hybridizes to the SARS-CoV-2 amplicon. In particular implementations, the nucleotide sequence of the probe comprises the sequence of SEQ ID NO:3 or SEQ ID NO:7. In some aspects, the probe is labeled with a fluorophore and a quencher of fluorescence of the fluorophore. The nucleic acid amplification may comprise calculating a Ct value or a Cq value.

In some embodiments, the biological sample comprises a nasopharyngeal swab sample or sputum. In some aspects, the biological sample is from a human.

In particular embodiments of the methods, two primer pairs are mixed with the biological sample. The sequence of one primer of the first primer pair consists essentially of: SEQ ID NO:1, SEQ ID NO:1 and a universal tail sequence, or SEQ ID NO:9. The sequence of the other primer of the first primer pair consists essentially of: SEQ ID NO:2, SEQ ID NO:2 and a universal tail sequence, or SEQ ID NO:10. The sequence of one primer of the second primer pair consists essentially of: SEQ ID NO:5, SEQ ID NO:5 and a universal tail sequence, or SEQ ID NO:11. The sequence of the other primer of the second primer pair consists essentially of: SEQ ID NO:6, SEQ ID NO:6 and a universal tail sequence, or SEQ ID NO:12. Where the sequence of one primer of the first primer pair consists essentially of SEQ ID NO:9 or SEQ ID NO:1 and a universal tail sequence; the sequence of the other primer of the first primer pair consists essentially of SEQ ID NO:10 or SEQ ID NO:2 and a universal tail sequence; the sequence of one primer of the second primer pair consists essentially of SEQ ID NO:11 or SEQ ID NO:5 and a universal tail sequence; and the sequence of the other primer of the second primer pair consists essentially of SEQ ID NO:12 or SEQ ID NO:6 and a universal tail sequence, the method may further comprise analyzing the nucleic acid amplification products by sequencing the nucleic acid amplification products using next-generation sequencing. Accordingly, the method also further comprises adding an index to the nucleic acid amplification products using at least one indexing oligonucleotide. In some aspects, the at least one indexing oligonucleotide comprises a complementary sequence that recognizes the universal tail sequence, SEQ ID NO:13, or SEQ ID NO:14.

In some implementations, the method of detecting SARS-CoV-2 in a subject may include the steps of adding to a mixture containing a sample from the subject, (a) a first forward primer comprising SEQ ID NO: 1, (b) a first reverse primer comprising SEQ ID NO: 2, (c) a second forward primer comprising SEQ ID NO: 5, and (d) a second reverse primer comprising SEQ ID NO: 6, subjecting the mixture to conditions that allow nucleic acid amplification, and detecting the presence or absence of SARS-CoV-2 by analyzing the nucleic acid amplification products. In various embodiments, the method further comprises adding to the mixture a detectably labeled first probe comprising SEQ ID NO: 3 and a detectably labeled second probe comprising SEQ ID NO: 7, and detecting the detectably labeled first probe and the detectably labeled second probe, thereby detecting the presence of SARS-CoV-2 in the subject. In various embodiments, the first forward primer and the second forward primer may further include a first universal tail sequence comprising SEQ ID NO: 13, and wherein the first reverse primer and the second reverse primer include a second universal tail sequence comprising SEQ ID NO: 14. The method may further comprise adding an index to the nucleic In various embodiments, the SARS-CoV-2 rRT-PCR assay comprises two forward primers (SEQ ID NO: 1 and SEQ ID NO: 5), two reverse primers (SEQ ID NO: 2 and SEQ ID NO: 6), and two probes (SEQ ID NO: 3 and SEQ ID NO: 7). The TG-N2 assay comprises a forward primer (SEQ ID NO: 1), a reverse primer (SEQ ID NO: 2) and a probe (SEQ ID NO: 3). The TG-spike4 assay comprises a forward primer (SEQ ID NO: 5), a reverse primer (SEQ ID NO: 6) and a probe (SEQ ID NO: 7).

TABLE 1 also shows sequences of the amplification products of the TG-N2 assay and the TG-spike4 assay. The amplicon produced using the TG-N2 assay (SEQ ID NO: 1 and SEQ ID NO: 2) has a sequence comprising SEQ ID NO: 4. The amplicon produced using the TG-spike4 assay (SEQ ID NO: 5 and SEQ ID NO: 6) has a sequence comprising SEQ ID NO: 8.

TABLE 1

| | Assay Component | Name | Sequence | SEQ ID NO: |
|---|---|---|---|---|
| N protein gene: TG-N2 assay | forward primer | TG-N2_F | TTCAGCGTTCTTCGGAATGTC | 1 |
| | reverse primer | TG-N2_R | TGGCACCTGTGTAGGTCAAC | 2 |
| | probe | TG-N2_FAMBHQ | CGCATTGGCATGGAAGTCACA CC | 3 |
| | amplicon sequence | amplicon sequence | TTCAGCGTTCTTCGGAATGTCG CGCATTGGCATGGAAGTCACA CCTTCGGGAACGTGGTTGACC TACACAGGTGCCA | 4 |
| S protein gene: TG-spike4 assay | forward primer | TG-spike4_F | CCAGTTGCTGTAGTTGTCTCAA G | 5 |
| | reverse primer | TG-spike4_R | CTGGCTCAGAGTCGTCTTCA | 6 |
| | probe | TG-spike4_FAMBHQ | TGTTGTTCTTGTGGATCCTGCT GC | 7 |
| | amplicon sequence | amplicon sequence | CCAGTTGCTG TAGTTGTCTC AAGGGCTGTT GTTCTTGTGG ATCCTGCTGC AAATTTGATG AAGACGACTC TGAGCCAG | 8 | acid amplification products using at least one indexing oligonucleotide. The method may further comprise analyzing the nucleic acid amplification products by sequencing the nucleic acid amplification products using next-generation sequencing.

TABLE 1 lists the primers and probes for a real-time PCR assays targeting the N protein gene and the spike protein gene of SARS-CoV-2. The "TG-N2" assay targets a 78 bp region of the N protein gene. The "TG-spike4" or "TG-54" assay targets a 77 bp region of the spike protein gene. While one assay (one primer pair and probes described herein) detects the presence or absence of SARS-CoV-2 virus, the use of two assays (two primer pairs and their respective probe) targeting different genes detects the presence or absence of SARS-CoV-2 virus with greater reliability than a single assay used alone. The TG-N2 assay and the TG-S4 assay (also referred to herein as the "SARS-CoV-2 rRT-PCR Assay") detect the presence or absence of SARS-CoV-2 virus with greater reliability than either the TG-N2 assay or the TG-S4 assay used alone. In further embodiments, two or more SARS-CoV-2 assays (primer pairs and probes), where at least one first assay targets the N protein gene of SARS-CoV-2 and where at least one second assay targets the spike protein gene of SARS-CoV-2, may detect the presence or absence of SARS-CoV-2 virus with greater reliability than an assay or combination of assays that target only one of the N protein gene or the S protein gene of SARS-CoV-2.

The preferred primers and probes described are designed for the specific detection of SARS-CoV-2. Each target on its own has been shown to provide sensitive and specific detection of SARS-CoV-2 with no detection of, or cross-reactivity to, other coronaviruses. Thus, the invention encompasses oligonucleotides of less than 40 nucleotides in length with nucleotide sequences of these oligonucleotides consisting of, consisting essentially of, or are "variants" of such preferred primers and probes. Thus, these oligonucleotides have a 5' terminus and a 3' terminus, recognize regions in the N protein gene or the S protein gene of SARS-CoV-2, and have a nucleotide sequence that consists essentially of, or is a variant of, the nucleotide sequence of: SEQ ID NO:1, SEQ ID NO:2, SEQ ID NO:3, SEQ ID NO:5, SEQ ID NO:6, or SEQ ID NO:7. As used herein, an oligonucleotide is a "variant" of another oligonucleotide if it retains the function of such oligonucleotide (e.g., acting as a specific primer or probe), but:

(1) lacks 1, 2, 3, 4, 5, 6, 7, 8, 9, or 10 nucleotides of the nucleotides of such primer or probe, or (2) lacks 1, 2, 3, 4, 5, 6, 7, 8, 9, or 10 of the 10 3' terminal nucleotides of such primer or probe, or (3) lacks 1, 2, 3, 4, 5, 6, 7, 8, 9, or 10 of the 10 5' terminal nucleotides of such primer or probe, or (4) has a sequence that differs from that of such primer or probe in having 1, 2, 3, 4, 5, 6, 7, 8, 9, 10 or more than 10 additional nucleotides, or (5) has a sequence that differs from that of such primer or probe in having 1, 2, 3, 4, 5, 6, 7, 8, 9, 10 or more than 10 substitution nucleotides in lieu of the nucleotides present in such primer or probe, or (6) possesses a combination of such (1)-(5).

In some aspects, the variant thereof has no more than 5 substitutions, deletions, or additions. In some embodiments, the oligonucleotide is modified with an internal spacer or a detectable label, for example, when the nucleotide sequence of the oligonucleotide comprises SEQ ID NO:3 or SEQ ID NO:7. In some embodiments, the 5' terminus is labeled with a fluorophore and the 3' terminus is complexed to a quencher of fluorescence of said fluorophore. In certain embodiments, the nucleotide sequence of the oligonucleotide further comprises a universal tail sequence, for example, a sequence selected from SEQ ID NO:13 and SEQ ID NO:14.

The disclose also provides kits for detecting SARS-CoV-2 in biological samples. A "kit," as used herein, refers to a combination of at least some items for performing a PCR assay for coronavirus detection, and more particularly coronavirus strain differentiation, and more particularly SAR-CoV-2 detection. Embodiments of kits may comprise one or more of the following reagents: at least one set of primers specific for SAR-CoV-2 detection, at least one probe specific for SAR-CoV-2 detection, internal positive control DNA to monitor presence of PCR inhibitors from various food and environmental sources, a baseline control, reagents for sample collection, reagents for isolating nucleic acid such as magnetic beads, spin columns, lysis buffers, proteases, reagents for PCR amplification such as a DNA polymerase or an enzymatically active mutant or variant thereof, reverse transcriptase, a DNA polymerase buffer, buffer containing dNTPs, deoxyribonucleotides dATP, dCTP, dGTP, or dTTP. In some embodiments, a probe is a TaqMa® probe. In certain kit embodiments, amplification primers are attached to a solid support such as a microarray. In some embodiments, a kit may include an internal control (for example, RNase P assay).

One or more kit components may be packaged in one or more container means. Kit container means may generally include at least one vial, test tube, flask, bottle, syringe or other packaging means, into which a component can be placed, and in some embodiments, suitably aliquoted. Where more than one component is included in a kit (they can be packaged together), the kit also will generally contain at least one second, third or other additional container into which the additional components can be separately placed.

However, various combinations of components can be packaged in a container means. Kits of the present teachings also will typically include reagent containers in close confinement for commercial sale. Such containers can include injection or blow-molded plastic containers into which the desired container means are retained. When the components of kits are provided in one and/or more liquid solutions, the liquid solution comprises an aqueous solution that can be a sterile aqueous solution.

In certain embodiments, at least one kit component is lyophilized and provided as dried powder(s). For example, primers and TaqMan® probes may be lyophilized. When reagents and/or components are provided as a dry powder, the powder can be reconstituted by the addition of a suitable solvent. In certain embodiments, a solvent is provided in another container means. Kits can also comprise an additional container means for containing a sterile, pharmaceutically acceptable buffer and/or other diluent.

A kit can also include instructions for employing the kit components as well as the use of any other reagent not included in the kit. Instructions can include variations that can be implemented. A kit may also contain an indication that links the output of the kit to a particular result. For example, an indication may be one or more sequences or that signify the identification of SARS-CoV-2. An indication may include a Ct value, wherein exceeding the Ct value indicates the presence or absence of an organism of interest. A kit may contain a positive control. A kit may contain a standard curve configured to quantify the amount of SARS-CoV-2 nucleic acid present in a sample. An indication includes any guide that links the output of the kit to a particular result. The indication may be a level of fluorescence or radioactive decay, a value derived from a standard curve, or from a control, or any combination of these and other outputs. The indication may be printed on a writing that may be included in the kit or it may be posted on the Internet or embedded in a software package.

In particular embodiments, the kit comprises a primer pair, wherein at least one primer of the primer pair consists of less than 40 nucleotides and has a nucleotide sequence that consists essentially of, or is a variant of, the nucleotide sequence of: SEQ ID NO:1, SEQ ID NO:2, SEQ ID NO:5, or SEQ ID NO:6, and wherein the primer pair is capable of detecting SARS-CoV-2, if present, in the sample by amplification; and SARS-CoV-2 detection reagents. In some aspects, the nucleotide sequence of the variant has no more than 5 substitutions, deletions, or additions when compared to the nucleotide sequence of SEQ ID NO:1, SEQ ID NO:2, SEQ ID NO:5, or SEQ ID NO:6. In some embodiments, the at least one of the primers of the primer pair is modified with an internal spacer or a detectable label. In certain embodiments, the kit further comprises a probe modified with an internal spacer or detectable label. The probe hybridizes to an oligonucleotide having a nucleotide sequence that consists essentially of SEQ ID NO:4 or SEQ ID NO:8. In some aspects, the probe is labeled with a fluorophore and a quencher of fluorescence of the fluorophore.

In particular embodiments of the kit, SEQ ID NO:1 and SEQ ID NO:2 make the primer pair. In other embodiments, SEQ ID NO:5 and SEQ ID NO:6 make the primer pair. In still other embodiments, the kit comprises two primer pairs, which are made of SEQ ID NO:1 and SEQ ID NO:2 for one pair and SEQ ID NO:5 and SEQ ID NO:6 for the other pair.

The kit may further comprise running buffer and a test strip. The test strip comprises filter paper and/or chitosan.

In particular embodiments, the kit comprises a first forward primer comprising SEQ ID NO: 1, a first reverse primer comprising SEQ ID NO: 2, a detectably labeled first probe comprising SEQ ID NO: 3, a second forward primer comprising SEQ ID NO: 5, a second reverse primer comprising SEQ ID NO: 6, a detectably labeled second probe comprising SEQ ID NO: 7, and optionally one or more PCR reagents. The first forward primer, the first reverse primer, the detectably labeled first probe, the second forward primer, the second reverse primer, the detectably labeled second probe, and the one or more PCR reagents may be lyophilized. The kit may further comprise an indication of a result that signifies the presence of SARS-CoV-2 and an indication of a result that signifies the absence of SARS-CoV-2. The result may comprise a Ct value or a Cq value.

In certain embodiments, the kit comprises two primer pairs. The sequence of one primer of the first primer pair consists essentially of: SEQ ID NO:1, SEQ ID NO:1 and a universal tail sequence, or SEQ ID NO:9. The sequence of the other primer of the first primer pair consists essentially of: SEQ ID NO:2, SEQ ID NO:2 and a universal tail sequence, or SEQ ID NO:10. The sequence of one primer of the second primer pair consists essentially of: SEQ ID NO:5, SEQ ID NO:5 and a universal tail sequence, or SEQ ID NO:11. The sequence of the other primer of the second primer pair consists essentially of: SEQ ID NO:6, SEQ ID NO:6 and a universal tail sequence, or SEQ ID NO:12.

EXAMPLES

The present invention is further illustrated by the following examples that should not be construed as limiting. The contents of all references, patents, and published patent applications cited throughout this application are incorporated herein by reference in their entirety for all purposes.
1. rRT-PCR with RNA Isolated Using Zymo Kit The exemplary assay is a rRT-PCR test to be run in conjunction with the RNase P assay developed by the Centers for Disease Control and Prevention (CDC) and published as part of their SARS-CoV-2 rRT-PCR detection kit.
a. Test Steps Clinical samples are processed using the following methods.

Nucleic acids are isolated and purified from nasopharyngeal specimens (swab specimen transport media, or nasopharyngeal aspirates or washes) using the Quick RNA Viral Kit (Zymo Research, catalog no. R1035). Specimen input volume is 100 and elution volume is 30 µL.

The purified nucleic acid is reverse transcribed into cDNA and subsequently amplified using Reliance One-Step Multiplex RT-qPCR Supermix (BioRad, catalog no. 12010220) and the SARS-CoV-2 primer/probe sets. This is performed in a 10 µL reaction containing 3 µL of purified RNA from a specimen on the CFX Connect Real-Time PCR Detection System (BioRad, catalog no. 1855200). In the process, the probe anneals to a specific target sequence located between the forward and reverse primers. During the extension phase of the PCR cycle, the 5' nuclease activity of Taq polymerase degrades the probe, causing the reporter dye to separate from the quencher dye, generating a fluorescent signal. With each cycle, additional reporter dye molecules are cleaved from their respective probes, increasing the fluorescence intensity exponentially. Fluorescence intensity is monitored at each PCR cycle by the CFX Connect Real-Time PCR Detection System using CFX Maestro Version 1.1 (BioRad, catalog no. 12004110).
b. Control Materials An extraction control comprised of the material from an unused nasopharyngeal sample collection device was used to identify any background or spurious signal that may have come from RNA extraction kit reagents or RNA extraction sample setup and interfered with accurate test result interpretation. The extraction control is used beside each set of samples for each RNA extraction procedure.

A negative extraction control (NEC) comprised of material from an unused nasopharyngeal specimen collection device, for example clean universal transport media (PBS), is processed alongside each batch of samples in the RNA extraction and PCR and is used to detect any background or spurious signal that may come from reagents or cross-contamination that may interfere with accurate test result interpretation.

A positive extraction control (PEC) comprised of a pool of material from remnant nasopharyngeal specimens (for example, PBS from nasopharyngeal swabs) validated to be negative for SARS-CoV-2 is processed alongside each batch of samples in the RNA extraction and PCR, and is used to determine that the lysate protocol and rRT-PCR assay are working as expected.

A negative template control (NTC) comprised of molecular grade, nuclease-free water, is added as template directly to a PCR reaction well for each primer/probe set for each rRT-PCR run. It is used to detect any background or spurious real-time PCR fluorescence or cross-contamination that may interfere with accurate interpretation of results from samples.

A positive SARS-CoV-2 template PCR control (PTC) is added as template directly to a PCR reaction well for each primer/probe set for each rRT-PCR run. The PTC is comprised of two in-vitro transcribed single stranded RNA sequences that are produced and precisely quantified at TGen North; it is run at two to four times the LoD of the assay to identify any loss of sensitivity of the SARS-CoV-2 rRT-PCR assay.

A positive RNase P template PCR control (PTC) is used to confirm that the RNase P internal control assay and thermal cycling are performing as expected and is used for each rRT-PCR run. The RNase P positive control is precisely quantified human genomic RNA obtained from Takara Bio, USA (Catalog No. 636524). This control is run at clinically relevant levels. The purpose overlaps with the positive extraction control but allows any potential irregularities to be isolated to the extraction process (PEC irregularity) or to the rRT-PCR process (RNase P template PCR control).

An internal control, comprised of the CDC's RNase P detection rRT-PCR assay contained in their validated SARS-CoV-2 assay set and detects human nucleic acids, is used to determine that each clinical specimen has sufficient human expression to preclude SARS-CoV-2 RNA within the patient sample.

TABLE 2 lists the concentrations of the primers and probes used in the exemplary assay.

TABLE 2

| Oligo Name | | Probe | rRT-PCR concentration (nM) |
|---|---|---|---|
| N protein gene: | TG-N2_F | | 450 |
| TG-N2 assay | TG-N2_R | | 450 |
| | TG-N2 | FAM-BHQ1 | 150 |
| S protein gene: | TG-spike4_F | | 450 |
| TG-spike4 assay | TG-spike4_R | | 450 |
| | TG-spike4 | FAM-BHQ1 | 150 |
| CDC's RNase P assay | MRP-F RNase P_F | | 450 |
| | MRP-R RNase P_R | | 450 |
| | MRP-P RNase P | FAM-BHQ1 | 150 | c. Control Results Interpretation and Quality Control Criteria

In embodiments where two or more assays are used in the detection of SARS-CoV-2, the following criteria are used to determine if the results are positive, negative, or undetermined.

All NTCs for an assay in a given rRT-PCR run must be negative, i.e., must yield no fluorescence signal that creates a Ct<40, to allow for interpretation of the results of any other assay. If any NTCs yield fluorescence signal that creates a Ct<40, the rRT-PCR run for that assay is invalid and the rRT-PCR test for all samples in that set across all assays must be repeated.

The positive SARS-CoV-2 PCR control must test positive for both the TG-N2 and TG-Spike4 primer and probe sets, i.e., must yield a Ct value <40, in a given rRT-PCR run to validate results of any other assay. If the positive control does not test positive, the rRT-PCR run for that assay is invalid and the rRT-PCR test for all samples in that set across all assays must be repeated.

The negative extraction control must test negative, i.e., must yield no fluorescence signal that creates a Ct<40, to validate the results of any samples processed (from RNA extraction) in the set with that extraction control. If any negative extraction controls yield fluorescence signal for any assay, all rRT-PCR assay results for that sample set are invalid and the RNA extraction and testing for all samples in that set must be repeated.

The positive extraction control must yield a Ct value ≤35 for the RNase P assay. Due to the nature of pooled negative samples, it is possible that samples with SARS-CoV-2 concentrations below our LoD will be included in the negative pool; thus, stochastic amplification with a Ct≥36 within the SARS-CoV-2 assays is considered valid. If the positive extraction control tests positive with a Ct<36 on either of the SARS-CoV-2 primer and probe sets, or Ct>35 on the RNase P assay, all rRT-PCR assay results for that sample set are invalid and the RNA extraction and testing of those samples must be repeated.

The internal control assay targeting the human RNase P RNA must yield a positive result (a Ct value ≤35) to validate a negative result for that sample. If any sample has a Ct>35 for RNase P the RNA extraction must be repeated for that specimen. If a specimen is extracted twice with both RNase P assays producing a Ct>35, the sample is considered inconclusive.

TABLE 3 shows expected performance of extraction and rRT-PCR positive and negative controls on the TG-N2, TG-SPIKE4, and RNase P rRT-PCR assays. *NR=not relevant.

i. Positive Result:

When all controls perform as expected, as outlined in TABLE 3, a specimen is considered positive for SARS-CoV-2 if the amplification curves produce a cycle threshold value less than 35 (Ct≤35) for one of the TGen assays and less than 40 (Ct<40) for the other assay with an internal control value (RNase P)≤35. A sample can also be considered positive if both (two of two) of the SARS-CoV-2 assays have amplification curves that produce cycle threshold values before 35 cycles (Ct≤35) with an internal control value (RNase P)≤35. A sample can also be considered positive if one of the two SARS-CoV-2 assays have amplification curves that produce cycle threshold values before 35 cycles (Ct≤35) and greater than or equal to 40 cycles (Ct≥40) or NaN for the other assay with an internal control value (RNase P)≤35 for two valid runs. Finally, a sample can be considered positive if the Ct values for both assays are between 35 and 40 cycles (35<Ct<40) with an internal control value (RNase P)≤35.

ii. Negative Result:

When all controls perform as expected, as outlined in TABLE 3, a specimen is considered negative for SARS-CoV-2 if amplification curves do not produce a cycle threshold value less than 40 (Ct<40) for both TG-N2 and TG-Spike4 primer and probe sets.

iii. Inconclusive Result:

When all controls perform as expected, as outlined in TABLE 3, a specimen is considered inconclusive if the RNase P gene amplification curves produce a cycle threshold after 35 cycles (Ct>35) or do not produce a Ct value (no amplification) after two valid tests. If the sample has only been tested on a single run, the sample is re-extracted from the original sample material. A specimen can also be considered inconclusive if a single (one of two) SARS-CoV-2 assays amplifies producing a cycle threshold value greater

TABLE 3

| CONTROL TYPE | USED TO MONITOR | TG-N2 | TG-SPIKE4 | RNASE P |
|---|---|---|---|---|
| NTC | Assay or rRT-PCR reagent contamination | No Ct, or Ct ≥ 40.0 | No Ct, or Ct ≥ 40.0 | No Ct, or Ct ≥ 40.0 |
| Synthesized Positive SARS-CoV-2 PCR Transcripts | Proper assay setup, reagent/assay integrity, rRT-PCR success | Ct < 40.0 | Ct < 40.0 | NR* |
| Positive Human gRNA PCR | Proper assay setup, reagent/assay integrity, rRT-PCR success | NR* | NR* | Ct ≤ 35.0 |
| RNase P gene in each clinical sample | Proper assay setup, reagent/assay integrity, rRT-PCR success | NR* | NR* | Ct ≤ 35.0 (for negative specimens) |
| Negative extraction control | RNA extraction kit reagent contamination, RNA extraction procedures | No Ct, or Ct ≥ 40.0 | No Ct, or Ct ≥ 40.0 | No Ct, or Ct ≥ 40.0 |
| Positive extraction control | RNA extraction success, specimen quality, rRT-PCR success | No Ct, or Ct ≥ 36.0 | No Ct, or Ct ≥ 36.0 | Ct ≤ 35.0 | d. Clinical Sample Results

In embodiments where two or more assays are used in the detection of SARS-CoV-2, the following criteria are used to determine if the results are positive, negative, or undetermined.

Assessment of clinical specimen test results will be performed after all positive/negative controls have been examined and determined to be valid as outlined in TABLE 3. If the controls are not valid, the patient results will not be interpreted. If all test controls perform as expected, the patient results will fall into one of four categories outlined below:

than or equal to 35 (Ct>35). A sample can also be considered inconclusive if one of the two SARS-CoV-2 assays have amplification curves that produce cycle threshold values before 35 cycles (Ct<35) and greater than or equal to 40 cycles (Ct≥40) or NaN for the other assay with an internal control value (RNase P)<35 for the first valid run and mismatched signals on a second valid run. Finally, a sample is considered inconclusive if the amplification curves produce a cycle threshold value that is greater than or equal to 35 and less than 40 (35≤Ct<40) for one of the TGen assays and greater than 40 (Ct≥40) or no amplification for the other assay with an internal control value (RNase P)<35.

TABLE 4

Assay results interpretation.

| RNase P | TG-N2 | TG-SPIKE4 | RESULT INTERPRETATION | DISCLAIMER/REPORT COMMENT |
|---|---|---|---|---|
| NA | Ct < 35.0 | Ct < 35.0 | Positive for SARS-CoV-2 | n/a |
| Ct ≤ 35.0 | Ct < 35.0 | Ct < 40.0 | Positive for SARS-CoV-2 | n/a |
| Ct ≤ 35.0 | Ct < 40.0 | Ct < 35.0 | Positive for SARS-CoV-2 | n/a |
| Ct ≤ 35.0 | 35 < Ct < 40 | 35 < Ct < 40 | Positive for SARS-CoV-2 | Late amplification; suggest recollection. |
| Ct ≤ 35.0 | Ct ≥ 40.0 or NaN | Ct ≥ 40.0 or NaN | Negative for SARS-CoV-2 | n/a |
| Ct > 35.0 on two runs | Ct ≥ 40.0 or NaN | Ct ≥ 40.0 or NaN | Inconclusive for SARS-CoV-2 | Inconclusive results may be due to insufficient RNA particles in the sample submitted. Recollection is recommended. |
| Ct ≤ 35.0 | 35.0 ≤ Ct < 40.0 | Ct ≥ 40.0 or NaN | Inconclusive for SARS-CoV-2 | Inconclusive results may be due to insufficient RNA particles in the sample submitted. Recollection is strongly recommended. |
| Ct ≤ 35.0 | Ct ≥ 40.0 or NaN | 35.0 ≤ Ct < 40.0 | Inconclusive for SARS-CoV-2 | Inconclusive results may be due to insufficient RNA particles in the sample submitted. Recollection is strongly recommended. |
| Ct ≤ 35.0 | Ct < 35.0 | Ct ≥ 40.0 or NaN | First valid run: Re-Run Second valid run (with same results OR both assays positive): Positive for SARS-CoV-2 Second valid run (with different results): Inconclusive for SARS-CoV-2 | If call is Positive: n/a If call is Inconclusive: Inconclusive results may be due to insufficient RNA particles in the sample submitted. Recollection is strongly recommended. |
| Ct ≤ 35.0 | Ct ≥ 40.0 or NaN | Ct < 35.0 | First valid run: Re-Run Second valid run (with same results OR both assays positive): Positive for SARS-CoV-2 Second valid run (with different results): Inconclusive for SARS-CoV-2 | If call is Positive: n/a If call is Inconclusive: Inconclusive results may be due to insufficient RNA particles in the sample submitted. Recollection is strongly recommended. | e. Validation Data

To validate and allow for interpretation of the results of any other assay, all no template PCR controls for an assay in a given rRT-PCR run need to be negative, i.e., yield no fluorescence signal that crosses the established assay threshold value. If any no template controls yield fluorescence signal that crosses the threshold, the rRT-PCR run for that assay is invalid and that test for all samples are repeated.

The positive PCR control must test positive for an assay (i.e. yield a Ct value below the established cutoff for that assay; in other words, emit fluorescent signal that crosses the established threshold for that assay before the thermal cycle number cutoff or Ct cutoff designated for each assay) in a given rRT-PCR run to validate results of any other assay. If the positive control does not test positive, that rRT-PCR run for that assay is invalid and that test for all samples are repeated.

The negative extraction control must test negative, i.e., yield no fluorescence signal that crosses the established assay threshold value for any assay, to validate the results of any samples processed (RNA extracted) in the set with that extraction control. If any negative extraction controls yield fluorescence signal for any assay, all rRT-PCR assay results for that sample set are invalid and the RNA extraction and testing for those samples are repeated.

The positive extraction control must test negative for both SARS-CoV-2 rRT-PCR Assay primer and probe sets, and positive for the RNase P assay. If the positive extraction control tests positive on either of the SARS-CoV-2 primer and probe sets, or negative on the RNase P assay, all rRT-PCR assay results for that sample set are invalid and the RNA extraction and testing for those samples are repeated.

The internal control assay targeting the human RNase P RNA must yield a positive result (for example, a Ct value<35, as is outlined in the CDC's test kit protocol) to validate all results for that sample, with one exception. If the sample tests positive for both SARS-CoV-2 rRT-PCR Assay primer and probe sets (TG-N2 and TG-spike4), the sample is considered positive. If any sample tests negative for RNase P and either or both of the SARS-CoV-2 rRT-PCR Assay primer and probe sets, that sample is reprocessed from RNA extraction through rRT-PCR testing. If a sample tests negative for RNase P on subsequent testing, it is reported as an invalid sample and no SARS-CoV-2 positive or negative diagnosis is given.

After all positive and negative PCR controls and internal controls have been analyzed and determined to be valid and acceptable, the clinical sample results are interpreted and analyzed.

i. Analytical Specificity

Primer and probe specificity was assessed across two in silico analyses. First, the primers and probes were checked for specificity to SARS-CoV-2 using nucleotide BLAST analysis of the National Center for Biotechnology Information (NCBI) nucleotide database. Second, the primers and probes were assessed for inclusivity of all SARS-CoV-2 published genomes. Results predicted that individual primers/probes did have interactions with other organisms; however, results for the overall assay did not show interactions with other organisms. The inclusivity analysis identified that by using two different targets (TG-N2 and TG-Spike4), the SARS-CoV-2 assay is expected to detect all currently published SARS-CoV-2 genomes.

Cross-reactivity was assessed by nucleotide BLAST analysis of the National Center for Biotechnology Information (NCBI) nucleotide database (accessed 03/06/2020). For the search query, "SARS2 (taxid: 2697049)" was excluded using the Organism filter, default parameters for short input sequences were used, and each SARS-CoV-2 rRT-PCR Assay component was included. The six SARS-CoV-2 complete genomes found in this database (not included in the taxid: 2697049 in the NCBI database) were removed from the list of results (and added to the Inclusivity results).

Cross-reactivity with organisms not in the NCBI database that may be present in human nasopharyngeal specimens were also assessed in silico. Shotgun metagenomic data of total RNA extractions from 9 nasopharyngeal specimens were used as a query to identify any sequence reads that aligned using the Burrows Wheeler Aligner (BWA) to the primers and probes in the SARS-CoV-2 rRT-PCR Assay (these shotgun data represent the "Pooled human nasal wash—to represent diverse microbial flora in the human respiratory tract" from the Recommended List of Organisms to be analyzed in silico or by Wet Testing TABLE 5). TABLE 5 lists the Recommended List of Organisms furnished by FDA to be analyzed in silico and results of in silico cross-reactivity evaluation.

TABLE 5

| Organism | Results |
|---|---|
| - High priority pathogens from the same genetic family - | |
| Human coronavirus 229E | No hits |
| Human coronavirus OC43 | No hits |
| Human coronavirus HKU1 | No hits |
| Human coronavirus NL63 | No hits |
| SARS-coronavirus | * |
| MERS-coronavirus | No hits |
| Human coronavirus 229E | No hits |
| - High priority organisms likely in circulating areas - | |
| Adenovirus (e.g. C1 Ad. 71) | No hits |
| Human Metapneumovirus (hMPV) | No hits |
| Parainfluenza virus 1-4 | No hits |
| Influenza A & B | No hits |
| Enterovirus (e.g. EV68) | No hits |
| Respiratory syncytial virus | No hits |
| Rhinovirus | No hits |
| Chlamydia pneumoniae | No hits |
| Haemophilus influenzae | No hits |
| Legionella pneumophila | No hits |
| Mycobacterium tuberculosis | No hits |
| Streptococcus pneumoniae | No hits |
| Streptococcus pyogenes | No hits |
| Bordetella pertussis | No hits |
| Mycoplasma pneumoniae | No hits |
| Pneumocystis jirovecii (PJP) | No hits |
| Pooled human nasal wash - to represent diverse microbial flora in the human respiratory tract | No hits |
| Candida albicans | TG-Spike4 probe hits at 95% identity |

TABLE 5-continued

| Organism | Results |
|---|---|
| Pseudomonas aeruginosa | TG-N2 forward primer hits two strains of "Pseudomonas sp." At 90% identity |
| Staphylococcus epidermis | No hits |
| Staphylococcus salivarius | No hits |

*See inclusivity analysis below for details regarding coverage across SARS-CoV-2 genomes.

Inclusivity was assessed for each of the TGen SARS-CoV-2 rRT-PCR primer/probe sets by use of the TGen in silico PCR pipeline. The TGen in silico PCR pipeline utilizes previously published SARS-CoV-2 genomes and screens primer and probe sequences across these genomes. If there was not an exact match to the primers and or probe, the genome was binned for further analysis. The analysis included 34,065 SARS-CoV-2 sequences. The TG-N2 primer and probe set had exact primer and probe matches to 33,533 genomes (98.4%, 95% CI: 98.3-98.6%). Of the 532 samples without an exact match, 131 had exactly 1 SNP difference between the genome and primers or probe. The TG-Spike4 assay had an exact match for 33,471 (98.3%, 95% CI: 98.1-98.4%) of the available sequences. Of the 594 samples without an exact match, 347 had exactly 1 SNP difference between the genome and primers or probe. Overall, 34,017 (99.9%, 95% CI: 99.8-99.9%) genomes had an exact match on at least one of the TGen SARS-CoV-2 primer/probe sets. A total of 48 genomes did not have an exact match for either primer/probe sets. Two of the 48 (4.2%, 95% CI: 0.7-15.4%). All of the other genomes had poor sequencing coverage across both of the primer/probe sets or poor coverage on one primer/probe set and a SNP in the other. Due to this analysis using large-scale published genomes (which inevitably include genomes with sequence errors and false coverage gaps), the design of two detection primer/probe sets, and primer/probe design with annealing and melting temperatures that would likely accommodate 1 or 2 sequence mismatches, the risk of a false-negative result when screening clinical samples is very low.

ii. Analytical Sensitivity.

A synthetic, single-stranded RNA control for both the TG-N2 and TG-Spike4 assays was synthesized. Both targets were quantified using a limiting dilution analysis and Poisson distribution. Quantified sRNA was spiked into SARS-CoV-2 negative remnant swab material and extracted and tested per TGen TNCL protocols. Results showed that the limit of detection (LoD) was 2.59 copies per µL PBS for TG-N2 and 1.67 copies per µL of PBS for TG-Spike4 assay.

The LoD was determined for each SARS-CoV-2 rRT-PCR Assay primer and probe set (TG-N2 and TG-Spike4) by serial dilution dynamic range studies using an in vitro-transcribed single-stranded RNA.

The LoD was determined by spiking 10 µL of the quantified in vitro-transcribed single-stranded RNA into 90 µL of negative matrix (PBS) at 15 different dilutions across the dynamic range of the SARS-CoV-2 primer/probe sets producing final concentrations of pooled transcripts ranging from $0.04$-$3.3\times10^4$ copies/µL for TG-N2 and $0.05$-$4.2\times10^4$ copies/µL for TG-Spike4. RNA from spiked matrix samples was individually extracted and underwent rRT-PCR. The LoD was determined by aggregating the results of the individual extraction replicates across two days and identifying the lowest concentration where at least 95% of the replicates (n>20) amplified. The lowest concentration at which 95% of replicates amplified was considered the LoD.

Results showed that the LoD was 2.59 copies per μL for TG-N2 (23/24 replicates, 96%) and 1.67 copies per μL for TG-Spike4 (23/24 replicates, 96%) (Tables 7, 8, Appendix 3). Additionally, a high degree of linearity was at concentrations 2.59-3.3×10⁴ copies/μL for TG-N2, R2=0.96, and from 1.6-4.2×10⁴ copies/μL for TG-Spike4, R2=0.96. Past the LoD (95% probability of detection), the probability of detection rapidly decreased for both the TG-N2 and the TG-Spike4 primer/probe sets (FIG. 1).

TABLE 7 depicts the aggregated data across days for RNase P, TG-N2, and TG-Spike4. The LoD was determined to be the dilution with at least 95% extraction replicate detection (n>20 total replicates) across days. The LoD for TG-N2 was determined to be at SS15 (2.59 copies per μL) and SS16 (1.67 copies per μL) for TG-Spike4. TABLE 8 depicts the aggregated data across dilutions for RNase P, TG-N2, and TG-Spike4.

TABLE 8-continued

Data reported as (SD, % CV) [n detected/total].

| Sample | Day 1 | | | Day 2 | | |
|---|---|---|---|---|---|---|
| Name | RNase P | TG-N2 | TG-Spike4 | RNase P | TG-N2 | TG-Spike4 |
| | 0.38%) | 0.2%) | 0.33%) | 0.31%) | 0.38%) | 3.55%) |
| | [3/3] | [3/3] | [3/3] | [3/3] | [3/3] | [6/6] |
| SS10 | 28.58 | 31.64 | 31.19 | 29.43 | 30.42 | 30.53 |
| | (0.26, | (0.17, | (0.44, | (0.17, | (0.26, | (0.61, |
| | 0.91%) | 0.54%) | 1.41%) | 0.58%) | 0.85%) | 2%) |
| | [3/3] | [3/3] | [3/3] | [6/6] | [6/6] | [9/9] |
| SS11 | 28.69 | 32.43 | 32.48 | 29.4 | 31.01 | 31.93 |
| | (0.14, | (0.28, | (0.21, | (0.21, | (0.28, | (0.85, |
| | 0.49%) | 0.86%) | 0.65%) | 0.71%) | 0.9%) | 2.66%) |
| | [6/6] | [6/6] | [6/6] | [3/3] | [3/3] | [9/9] |

TABLE 7

Data reported as (SD, % CV) [n detected/total].

| Sample Name | Aggregate RNase P | TG-N2 | | TG-Spike4 | |
|---|---|---|---|---|---|
| | | Copies/ μL | Aggregated Results | Copies/ μL | Aggregated Results |
| SS05 | 29.1 (0.73, 2.51%) [4/4] | 33113.41 | 22.22 (0.11, 0.5%) [4/4] | 42837.81 | 22.14 (0.19, 0.86%) [4/4] |
| SS07 | 29.24 (0.63, 2.15%) [6/6] | 331.13 | 28.69 (0.9, 3.14%) [6/6] | 428.38 | 28.47 (0.96, 3.37%) [6/6] |
| SS09 | 29.04 (0.45, 1.55%) [6/6] | 165.57 | 29.86 (0.88, 2.95%) [6/6] | 214.19 | 29.55 (1.05, 3.55%) [6/6] |
| SS10 | 29.15 (0.46, 1.58%) [9/9] | 82.78 | 30.83 (0.65, 2.11%) [9/9] | 107.09 | 30.53 (0.61, 2%) [9/9] |
| SS11 | 28.93 (0.39, 1.35%) [9/9] | 41.39 | 31.95 (0.75, 2.35%) [9/9] | 53.55 | 31.93 (0.85, 2.66%) [9/9] |
| SS12 | 29.13 (0.56, 1.92%) [12/12] | 20.70 | 32.95 (0.55, 1.67%) [12/12] | 26.77 | 33.13 (0.79, 2.38%) [12/12] |
| SS13 | 28.97 (0.59, 2.04%) [9/9] | 10.35 | 34.34 (1.02, 2.97%) [9/9] | 13.39 | 34.27 (1.13, 3.3%) [9/9] |
| SS14 | 28.99 (0.55, 1.9%) [17/17] | 5.17 | 35.25 (0.52, 1.48%) [17/17] | 6.69 | 35.01 (0.53, 1.51%) [17/17] |
| SS15 | 29.02 (0.37, 1.27%) [24/24] | 2.59 (LoD) | 36.01 (0.72, 2%) [23/24] | 3.35 | 35.81 (0.75, 2.09%) [23/24] |
| SS16 | 29.04 (0.41, 1.41%) [24/24] | 1.29 | 36.76 (0.61, 1.66%) [22/24] | 1.67 (LoD) | 36.57 (0.68, 1.86%) [23/24] |
| SS17 | 29.38 (1.43, 4.87%) [21/21] | 0.65 | 36.81 (0.66, 1.79%) [15/21] | 0.84 | 37.16 (0.75, 2.02%) [12/21] |
| SS18 | 29.18 (0.52, 1.78%) [17/17] | 0.32 | 37.09 (0.49, 1.32%) [12/17] | 0.42 | 37.77 (0.29, 0.77%) [9/17] |
| SS19 | 29.24 (0.76, 2.6%) [9/9] | 0.16 | 36.95 (1.07, 2.9%) [3/9] | 0.21 | 37.4 (0.85, 2.27%) [4/9] |
| SS20 | 28.97 (0.6, 2.07%) [6/6] | 0.08 | NaN [0/6] | 0.10 | 37.77 (NA, NA %) [1/6] |
| SS21 | 29.31 (0.04, 0.14%) [3/3] | 0.04 | NaN [0/3] | 0.05 | 38.62 (NA, NA %) [1/3] |

TABLE 8

Data reported as (SD, % CV) [n detected/total].

| Sample | Day 1 | | | Day 2 | | |
|---|---|---|---|---|---|---|
| Name | RNase P | TG-N2 | TG-Spike4 | RNase P | TG-N2 | TG-Spike4 |
| SS05 | 28.46 | 22.13 | 21.97 | 29.73 | 22.3 | 22.14 |
| | (0.02, | (0.05, | (0.01, | (0.06, | (0.09, | (0.19, |
| | 0.07%) | 0.23%) | 0.05%) | 0.2%) | 0.4%) | 0.86%) |
| | [2/2] | [2/2] | [2/2] | [2/2] | [2/2] | [4/4] |
| SS07 | 28.67 | 29.5 | 29.34 | 29.8 | 27.88 | 28.47 |
| | (0.1, | (0.14, | (0.09, | (0.13, | (0.12, | (0.96, |
| | 0.35%) | 0.47%) | 0.31%) | 0.44%) | 0.43%) | 3.37%) |
| | [3/3] | [3/3] | [3/3] | [3/3] | [3/3] | [6/6] |
| SS09 | 28.64 | 30.66 | 30.5 | 29.44 | 29.06 | 29.55 |
| | (0.11, | (0.06, | (0.1, | (0.09, | (0.11, | (1.05, |

TABLE 8-continued

Data reported as (SD, % CV) [n detected/total].

| Sample | Day 1 | | | Day 2 | | |
|---|---|---|---|---|---|---|
| Name | RNase P | TG-N2 | TG-Spike4 | RNase P | TG-N2 | TG-Spike4 |
| SS12 | 28.65 | 33.36 | 33.76 | 29.61 | 32.54 | 33.13 |
| | (0.26, | (0.32, | (0.33, | (0.26, | (0.39, | (0.79, |
| | 0.91%) | 0.96%) | 0.98%) | 0.88%) | 1.2%) | 2.38%) |
| | [6/6] | [6/6] | [6/6] | [6/6] | [6/6] | [12/12] |
| SS13 | 28.6 | 34.92 | 34.98 | 29.7 | 33.17 | 34.27 |
| | (0.19, | (0.63, | (0.46, | (0.28, | (0.29, | (1.13, |
| | 0.66%) | 1.8%) | 1.32%) | 0.94%) | 0.87%) | 3.3%) |
| | [6/6] | [6/6] | [6/6] | [3/3] | [3/3] | [9/9] |

TABLE 8-continued

| | Day 1 | | | Day 2 | | |
|---|---|---|---|---|---|---|
| Sample Name | RNase P | TG-N2 | TG-Spike4 | RNase P | TG-N2 | TG-Spike4 |
| SS14 | 28.64 (0.21, 0.73%) [11/11] | 35.41 (0.35, 0.99%) [11/11] | 35.14 (0.46, 1.31%) [11/11] | 29.63 (0.36, 1.21%) [6/6] | 34.96 (0.68, 1.95%) [6/6] | 35.01 (0.53, 1.51%) [17/17] |
| SS15 | 28.66 (0.14, 0.49%) [11/11] | 36.14 (0.64, 1.77%) [11/11] | 36.29 (0.56, 1.54%) [10/11] | 29.32 (0.17, 0.58%) [13/13] | 35.89 (0.79, 2.2%) [12/13] | 35.81 (0.75, 2.09%) [23/24] |
| SS16 | 28.66 (0.2, 0.7%) [11/11] | 36.72 (0.52, 1.42%) [9/11] | 36.55 (0.84, 2.3%) [10/11] | 29.36 (0.2, 0.68%) [13/13] | 36.79 (0.68, 1.85%) [13/13] | 36.57 (0.68, 1.86%) [23/24] |
| SS17 | 28.63 (0.24, 0.84%) [8/8] | 36.28 (0.56, 1.54%) [6/8] | 36.98 (0.93, 2.51%) [4/8] | 29.85 (1.67, 5.59%) [13/13] | 37.17 (0.46, 1.24%) [9/13] | 37.16 (0.75, 2.02%) [12/21] |
| SS18 | 28.6 (0.33, 1.15%) [6/6] | 36.99 (0.51, 1.38%) [4/6] | 38.07 (0.34, 0.89%) [2/6] | 29.5 (0.25, 0.85%) [11/11] | 37.14 (0.51, 1.37%) [8/11] | 37.77 (0.29, 0.77%) [9/17] |
| SS19 | 28.26 (0.09, 0.32%) [3/3] | 35.73 (NA, NA %) [1/3] | 36.89 (0.81, 2.2%) [2/3] | 29.73 (0.27, 0.91%) [6/6] | 37.57 (0.06, 0.16%) [2/6] | 37.4 (0.85, 2.27%) [4/9] |
| SS20 | 28.44 (0.11, 0.39%) [3/3] | NaN [0/3] | NaN [0/3] | 29.51 (0.19, 0.64%) [3/3] | NaN [0/3] | 37.77 (NA, NA %) [1/6] |
| SS21 | No Samples Tested | No Samples Tested | No Samples Tested | 29.31 (0.04, 0.14%) [3/3] | NaN [0/3] | 38.62 (NA, NA %) [1/3] | iii. Precision

A synthetic single-stranded RNA control for the TG-N2 and TG-Spike4 was spiked into SARS-CoV-2 negative remnant swab material at four different dilutions (SS10, SS14, SS15, and SS16) and frozen. Aliquots were extracted and tested per TNCL protocols in duplicate across 9 batches. Results identified consistent Ct values across a total of 9 runs with a higher standard deviation compared to the analytical sensitivity validation.

Figure 2:
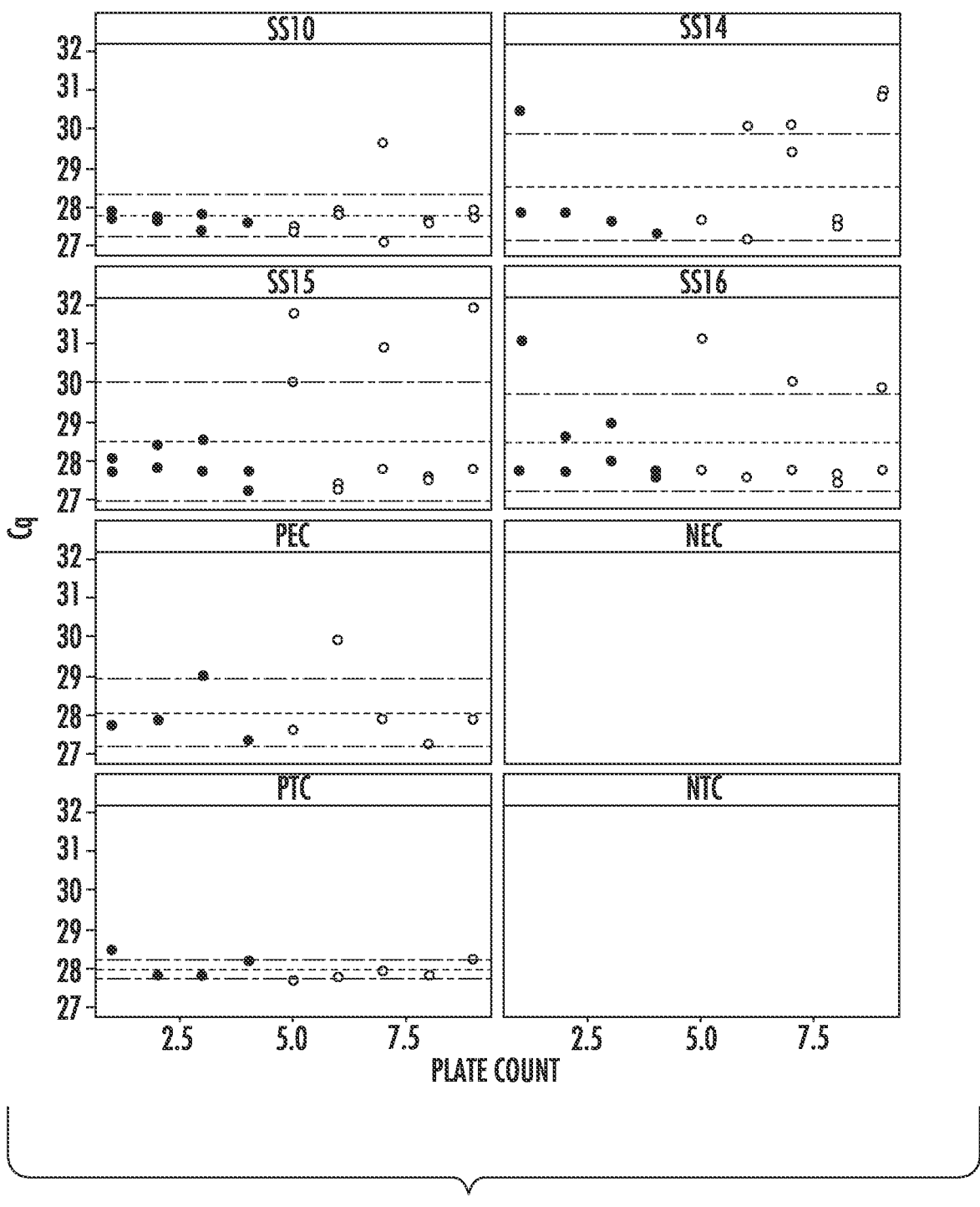
FIG. 2 depicts the Ct values of contrived samples and controls across 9 batches for RNase P. Black line indicates mean and blue lines indicate +/−1 standard deviation.
Figure 3:
FIG. 3 depicts the Ct values of contrived samples and controls across 9 batches for TG-N2. Black line indicates mean and blue lines indicate +/−1 standard deviation.
Figure 4:
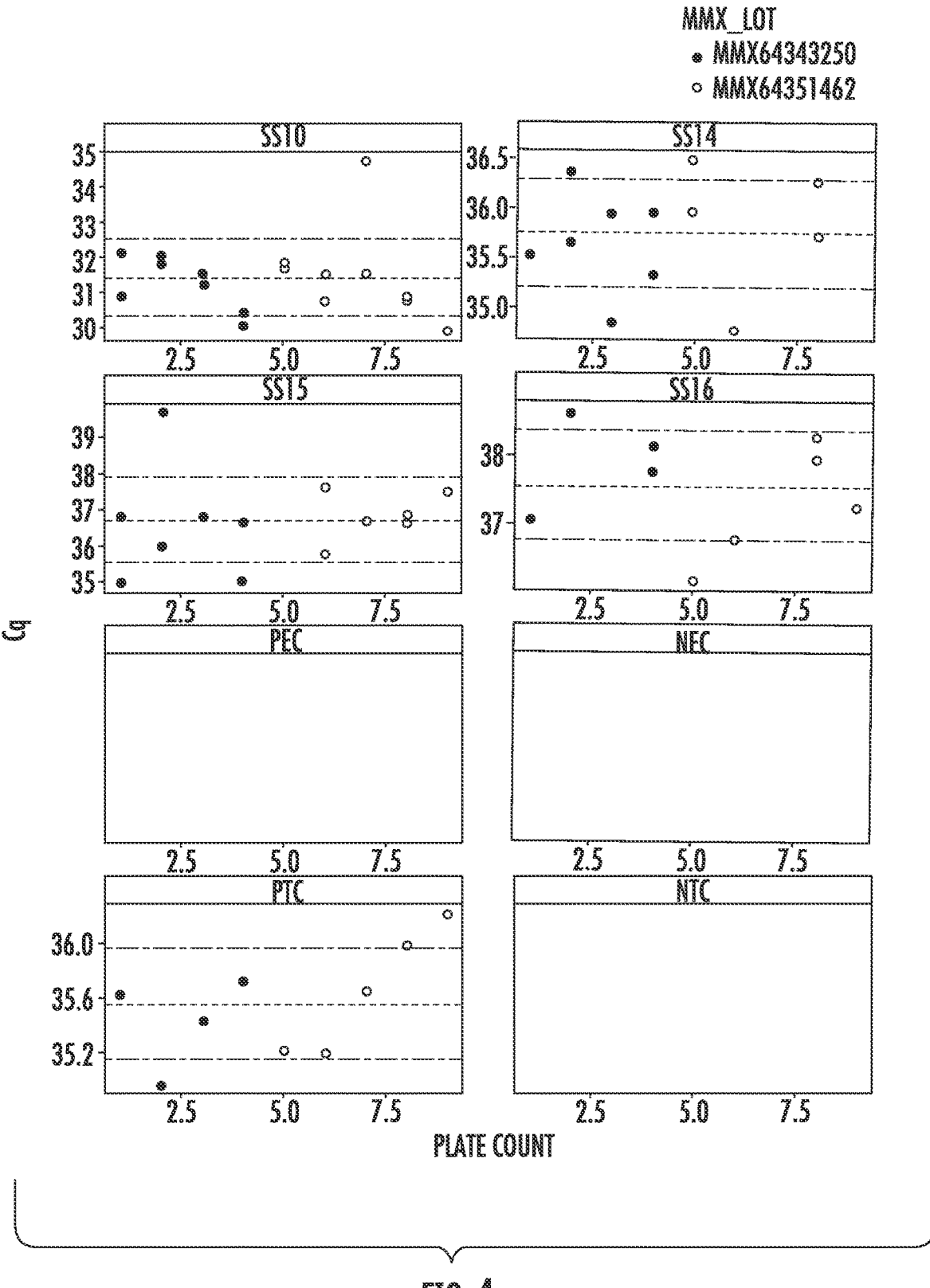
FIG. 4 depicts Ct values of contrived samples and controls across 9 batches for TG-Spike4. Black line indicates mean and blue lines indicate +/−1 standard deviation.

The precision study was conducted by combining 4.5 mL of pooled remnant swab material, 5 mL of DNA/RNA Shield (Zymo, Cat no: R1100-250), and 500 µL of transcription product. 200 µL aliquots were frozen and processed per TGen North Protocols. Results identified consistent Ct values across each batch (FIGS. 2-4; TABLE 9). Due to low concentration samples going through a freeze thaw, reproducibility was lowered at our LoD to 72% for the TG-N2 assay and 50% for the TG-Spike4 assay. This discrepancy is likely due to the stochastic nature of loss of RNA at low concentrations. Summary data for each dilution and control are available in TABLE 9.

TABLE 9

| | TG-N2 Copies per µL | TG-Spike4 Copies per µL | CDC-RP | TG-N2 | TG-S4 |
|---|---|---|---|---|---|
| Sample | | | | | |
| SS10 | 82.78 | 107.09 | 27.78 (0.5, 1.8%) [18/18] | 31.28 (1.23, 3.93%) [18/18] | 31.41 (1.1, 3.5%) [17/18] |

TABLE 9-continued

| | TG-N2 Copies per µL | TG-Spike4 Copies per µL | CDC-RP | TG-N2 | TG-S4 |
|---|---|---|---|---|---|
| Sample | | | | | |
| SS14 | 5.17 | 6.69 | 28.51 (1.34, 4.7%) [18/18] | 36.01 (1.25, 3.47%) [15/18] | 35.73 (0.55, 1.54%) [12/18] |
| SS15 | 2.59 | 3.35 | 28.52 (1.51, 5.29%) [18/18] | 36.26 (0.83, 2.29%) [13/18] | 36.71 (1.16, 3.16%) [14/18] |
| SS16 | 1.29 | 1.67 | 28.45 (1.21, 4.25%) [18/18] | 36.82 (1.11, 3.01%) [10/18] | 37.52 (0.8, 2.13%) [9/18] |
| PEC | NA | NA | 28.05 (0.85, 3.03%) [9/9] | NaN (NA, NA %) [0/9] | NaN (NA, NA %) [0/9] |
| NEC | NA | NA | NaN (NA, NA %) [0/9] | NaN (NA, NA %) [0/9] | NaN (NA, NA %) [0/9] |
| PTC | NA | NA | 27.97 (0.25, 0.89%) [9/9] | 33.41 (0.72, 2.16%) [9/9] | 35.55 (0.4, 1.13%) [9/9] |
| NTC | NA | NA | NaN (NA, NA %) [0/9] | NaN (NA, NA %) [0/9] | NaN (NA, NA %) [0/9] | iv. Accuracy 30 positive and 30 negative specimens were tested. This assay achieved 97% concordance using the above testing method (104, reactions), with 97% sensitivity and specificity.

The accuracy evaluation of the SARS-CoV2 rRT-PCR Assay was conducted through blind testing of 30 positive and 30 negative remnant nasopharyngeal, nasal, and oral SARS-CoV-2 swab samples that were originally tested by the Arizona State Public Health Laboratory (CLIA Number: 03D0641866).

Results showed that the SARS-CoV2 rRT-PCR Assay successfully identified 29/30 (97%) positive samples (TABLE 10). The one discrepant sample was retested by the SARS-CoV2 rRT-PCR and later identified a positive result (Clinical Evaluation #52). 97% (29/30) of negative samples were also identified as true negatives. The one discrepant sample was retested and again maintained a positive result, with the TG-SPIKE4 assay detecting SARS-CoV-2 RNA. This discrepancy could be due to the TGen SARS-CoV2 rRT-PCR detecting two separate genes (N and S gene) compared to the Arizona State Public Health Laboratory which uses two separate assays to detect a single viral gene (N gene) (Clinical Evaluation #26). TABLE 10 summarizes the clinical evaluation comparing the SARS-CoV2 rRT-PCR Assay to 30 positive and 30 negative samples.

TABLE 10

|  | Positive (97%) | Negative (97%) | Total |
|---|---|---|---|
| Positive | 29 | 1* | 30 |
| Negative | 1** | 29 | 30 |
| Total | 30 | 30 |  |

*Clinical Evaluation #52 was initially identified as negative; however, subsequent extraction and testing revealed positive results.
**Clinical Evaluation #26 was initially identified as positive due to TG-Spike4 amplification; subsequent extraction and testing confirmed this positive result.

f. Additional Validation for Alternative Specimens and Mastermix

Saliva has been shown to have a similar or even higher diagnostic sensitivity to nasopharyngeal samples. This validation is based on using a Spectrum SDNA-1000 kit. This kit allows the user to transfer a saliva sample (~2 mL) into the collection kit with the use of a plastic screw on funnel. After the saliva sample is collected, the funnel is removed, and the cap of the device is screwed on. After tightening of the cap, a seal within the cap is broken and the preservative liquid is mixed with the sample. At this time the tube is inverted several times and can be stored at room temperature prior to laboratory processing.

i. Confirmation of Analytical Sensitivity

Confirmation of analytical sensitivity was performed by using pooled, negative, Spectrum saliva samples and spiking synthetic transcribed RNA into these samples. More than 20 replicates were processed at the nasopharyngeal LoD (SS15, TG-N2: 2.59 copies per $\mu$L & TG-Spike4: 3.35 copies per $\mu$L). These replicates were then extracted and screened with the TGen SARS-CoV-2 Assay to ensure at least 95% of the replicates had amplification. At SS15, 21/22 (95.5%) replicates amplified, confirming similar analytical sensitivity relative to the nasopharyngeal samples (TABLE 11).

TABLE 11

Data are reported as mean (SD, % CV) [n detected/total].

| Sample | CDC-RP | TG-N2 | TG-SPIKE4 |
|---|---|---|---|
| SS14 | 24.78 (0.03, 2.06%) [2/2] | 34.95 (0.37, 25.88%) [2/2] | 34.13 (0.49, 34.7%) [2/2] |
| SS15 (TG-N2: 2.59 c/$\mu$L, TG-Spike4: 3.35 c/$\mu$L) | 24.89 (1.92, 217.47%) [22/22] | 35 (1.03, 80.79%) [21/22] | 35.23 (0.65, 47.06%) [21/22] |
| PEC | 27.65 (0.2, 13.83%) [3/3] | NaN (NA, NA %) [0/3] | NaN (NA, NA %) [0/3] |
| NEC | NaN (NA, NA %) [0/3] | NaN (NA, NA %) [0/3] | NaN (NA, NA %) [0/3] |
| PTC | 28.27 (0.21, 14.53%) [3/3] | 34.41 (1.15, 93.3%) [3/3] | 36.04 (1.39, 122.33%) [3/3] |
| NEC | NaN (NA, NA %) [0/3] | NaN (NA, NA %) [0/3] | NaN (NA, NA %) [0/3] | ii. Clinical Evaluation (Accuracy)

A total of 46 remnant TNCL clinical saliva samples in Spectrum reagent were tested with the TGen SARS-CoV-2 Assay. Overall, results showed 89.1% concordance between Spectrum saliva specimens run through the TNCL SARS-CoV-2 rRT-PCR Assay and co-collected NP specimens run through either the TNCL SARS-CoV-2 rRT-PCR Assay or the TNCL SARS-CoV-2 Direct Assay. The loss of sensitivity was observed near and beyond the limit of detection of the TNCL SARS-CoV-2 rRT-PCR and TNCL SARS-CoV-2 Direct Assays.

Samples used for this validation included TNCL saliva specimens originally collected in Spectrum reagent (n=26) and co-collected alongside NP specimens (n=26), and TNCL saliva specimens manually contrived with Spectrum reagent (n=20) and co-collected alongside NP specimens (n=20). For contrived Spectrum saliva specimens, 70 $\mu$L of sample was added to 52.5 $\mu$L Spectrum reagent to produce a 0.75× ratio of Spectrum reagent to saliva specimen. Original Spectrum specimens and associated, co-collected NP specimens were extracted using the TNCL SARS-CoV-2 rRT-PCR Assay. Contrived Spectrum saliva specimens were also extracted using the TNCL SARS-CoV-2 rRT-PCR Assay, while associated, co-collected NP specimens were extracted using the TNCL SARS-CoV-2 Direct Assay. Overall, results showed 89.1% concordance between Spectrum saliva specimens and co-collected NP specimens, with 84% concordance between co-collections where at least one sample was positive and 95% concordance where at least one sample was negative (TABLE 12). Concordance was higher among original Spectrum specimens and associated, co-collected NP specimens, as both specimen types were extracted using the TNCL SARS-CoV-2 rRT-PCR Assay, which is more sensitive than the TNCL SARS-CoV-2 Direct Assay. Furthermore, sensitivity was lost near and beyond the limit of detection for both assays, irrespective of specimen type.

TABLE 12 presents a confusion matrix for clinical evaluation between saliva collected in Spectrum reagent and NP specimens.

TABLE 12

|  | Positive | Negative | Inconclusive |
|---|---|---|---|
| Positive | 21 | 1 | 0 |
| Negative | 0 | 20 | 0 |
| Inconclusive | 3 | 1 | 0 |

2. rRT-PCR with Directly Isolated RNA (Crude RNA)

The exemplary assay is a rRT-PCR test to be run in conjunction with the RNase P assay developed by the Centers for Disease Control and Prevention (CDC) and published as part of their SARS-CoV-2 rRT-PCR detection kit. The TGen SARS-CoV-2 primer and probe sets are designed to detect RNA from the SARS-CoV-2 virus in respiratory specimens from patients as recommended for testing by public health authority guidelines.

a. Test Steps

Clinical samples are processed with a simple Proteinase K extraction and incubated for 5 minutes at 95° C.

3 $\mu$l of lysate is reverse transcribed into cDNA and subsequently amplified using Reliance One-Step Multiplex RT-qPCR Supermix (BioRad, catalog no. 12010220) and the TGen SARS-CoV-2 primer/probe sets. This is performed in a 10 $\mu$L reaction containing 3 $\mu$L of lysate from a specimen, on the CFX Connect Real-Time PCR Detection System (BioRad, catalog no. 1855200). In the process, the probe anneals to a specific target sequence located between the forward and reverse primers. During the extension phase of the PCR cycle, the 5' nuclease activity of Taq polymerase degrades the probe, causing the reporter dye to separate from the quencher dye to generate a fluorescent signal. With each cycle, additional reporter dye molecules are cleaved from their respective probes, increasing the fluorescence intensity exponentially. Fluorescence intensity is monitored at each PCR cycle by the CFX Connect Real-Time PCR Detection System using CFX Maestro Version 1.1 (BioRad, catalog no. 12004110).

b. Control Materials

A negative extraction control (NEC) comprised of material from an unused nasopharyngeal specimen collection device, for example clean universal transport media (PBS), is processed alongside each batch of samples in the RNA extraction and PCR and is used to detect any background or spurious signal that may come from reagents or cross-contamination that may interfere with accurate test result interpretation.

A positive extraction control (PEC) comprised of a pool of material from remnant nasopharyngeal specimens (for example, PBS from nasopharyngeal swabs) validated to be negative for SARS-CoV-2 is processed alongside each batch of samples in the RNA extraction and PCR and is used to determine that the lysate protocol and rRT-PCR assay are working as expected.

A negative template control (NTC) comprised of molecular grade, nuclease-free water, is added as template directly to a PCR reaction well for each primer/probe set for each rRT-PCR run. It is used to detect any background or spurious real-time PCR fluorescence or cross-contamination that may interfere with accurate interpretation of results from samples.

A positive SARS-CoV-2 template PCR control (PTC) is added as template directly to a PCR reaction well for each primer/probe set for each rRT-PCR run. The PTC is comprised of two in-vitro transcribed single stranded RNA sequences that are produced and precisely quantified at TGen North; it is run at two to four times the LoD of the assay to identify any loss of sensitivity of the SARS-CoV-2 rRT-PCR assay.

A positive RNase P template PCR control (PTC) is used to confirm that the RNase P internal control assay and thermal cycling are performing as expected and is used for each rRT-PCR run. The RNase P positive control is precisely quantified human genomic RNA obtained from Takara Bio, USA (Catalog No. 636524). This control is run at clinically relevant levels. The purpose overlaps with the positive extraction control but allows any potential irregularities to be isolated to the extraction process (PEC irregularity) or to the rRT-PCR process (RNase P template PCR control).

An internal control, comprised of the CDC's RNase P detection rRT-PCR assay contained in their validated SARS-CoV-2 assay set and detects human nucleic acids, is used to determine that each clinical specimen has sufficient human expression to preclude SARS-CoV-2 RNA within the patient sample.

The same concentrations of the primers and probes are used in this example as in Example 1 (see TABLE 2 for concentrations).

c. Control Results Interpretation and Quality Control Criteria

All NTCs for an assay in a given rRT-PCR run must be negative, i.e., must yield no fluorescence signal that creates a Ct<40, to allow for interpretation of the results of any other assay. If any NTCs yield fluorescence signal that creates a Ct<40, the rRT-PCR run for that assay is invalid and the rRT-PCR test for all samples in that set across all assays must be repeated.

The positive SARS-CoV-2 PCR control must test positive for both the TG-N2 and TG-Spike4 primer and probe sets, i.e., must yield a Ct value<40, in a given rRT-PCR run to validate results of any other assay. If the positive control does not test positive, the rRT-PCR run for that assay is invalid and the rRT-PCR test for all samples in that set across all assays must be repeated.

The negative extraction control must test negative, i.e., must yield no fluorescence signal that creates a Ct<40, to validate the results of any samples processed (from RNA extraction) in the set with that extraction control. If any negative extraction controls yield fluorescence signal for any assay, all rRT-PCR assay results for that sample set are invalid and the RNA extraction and testing for all samples in that set must be repeated.

The positive extraction control must yield a Ct value ≤35 for the RNase P assay. Due to the nature of pooled negative samples, it is possible that samples with SARS-CoV-2 concentrations below our LoD will be included in the negative pool; thus, stochastic amplification with a Ct≥36 within the SARS-CoV-2 assays is considered valid. If the positive extraction control tests positive with a Ct<36 on either of the SARS-CoV-2 primer and probe sets, or Ct>35 on the RNase P assay, all rRT-PCR assay results for that sample set are invalid and the RNA extraction and testing of those samples must be repeated.

The internal control assay targeting the human RNase P RNA must yield a positive result (a Ct value ≤35) to validate a negative result for that sample. If any sample has a Ct>35 for RNase P the RNA extraction must be repeated for that specimen. If a specimen is extracted twice with both RNase P assays producing a Ct>35, the sample is considered inconclusive.

As with Example 1, TABLE 3 above shows expected performance of extraction and rRT-PCR positive and negative controls on the TG-N2, TG-SPIKE4, and RNase P rRT-PCR assays.

d. Clinical Sample Results

Assessment of clinical specimen test results will be performed after all positive/negative controls have been examined and determined to be valid as outlined in TABLE 3. If the controls are not valid, the patient results will not be interpreted. As in Example 1, TABLE 4 lists the assay results interpretation guide. If all test controls perform as expected, the patient results will fall into one of four categories outlined below:

i. Positive Result:

When all controls perform as expected, as outlined in TABLE 3, a specimen is considered positive for SARS-CoV-2 if the amplification curves produce a cycle threshold value less than 35 (Ct≤35) for one of the TGen assays and less than 40 (Ct<40) for the other assay with an internal control value (RNase P)≤35. A sample can also be considered positive if both (two of two) of the SARS-CoV-2 assays have amplification curves that produce cycle threshold values before 35 cycles (Ct≤35) with an internal control value (RNase P)≤35. A sample can also be considered positive if one of the two SARS-CoV-2 assays have amplification curves that produce cycle threshold values before 35 cycles (Ct≤35) and greater than or equal to 40 cycles (Ct≥40) or NaN for the other assay with an internal control value (RNase P)≤35 for two valid runs. Finally, a sample can be considered positive if the Ct values for both assays are between 35 and 40 cycles (35<Ct<40) with an internal control value (RNase P)≤35.

ii. Negative Result:

When all controls perform as expected, as outlined in TABLE 3, a specimen is considered negative for SARS-CoV-2 if amplification curves do not produce a cycle threshold value less than 40 (Ct<40) for both TG-N2 and TG-Spike4 primer and probe sets.

iii. Inconclusive Result:

When all controls perform as expected, as outlined in TABLE 3, a specimen is considered inconclusive if the RNase P gene amplification curves produce a cycle threshold after 35 cycles (Ct>35) or do not produce a Ct value (no amplification) after two valid tests. If the sample has only been tested on a single run, the sample is re-extracted from the original sample material. A specimen can also be considered inconclusive if a single (one of two) SARS-CoV-2 assays amplifies producing a cycle threshold value greater than or equal to 35 (Ct>35). A sample can also be considered inconclusive if one of the two SARS-CoV-2 assays have amplification curves that produce cycle threshold values before 35 cycles (Ct<35) and greater than or equal to 40 cycles (Ct≥40) or NaN for the other assay with an internal control value (RNase P)<35 for the first valid run and mismatched signals on a second valid run. Finally, a sample is considered inconclusive if the amplification curves produce a cycle threshold value that is greater than or equal to 35 and less than 40 (35≤Ct<40) for one of the TGen assays and greater than 40 (Ct≥40) or no amplification for the other assay with an internal control value (RNase P)<35.

e. Validation Data i. Analytical Specificity

The validation data with regard to analytical specificity of Example 1 applies here.

ii. Analytical Sensitivity.

Heat-inactivated SARS-CoV-2 was serially diluted into remnant clinical PBS. Several replicates of 50 μL of spiked samples were processed with the Proteinase K extraction process and both rRT-PCR targets tested per TGen TNCL protocols. Results showed that the limit of detection was 3.13 genomes per μL for TG-N2 and TG-Spike4 assay.

Figure 5:
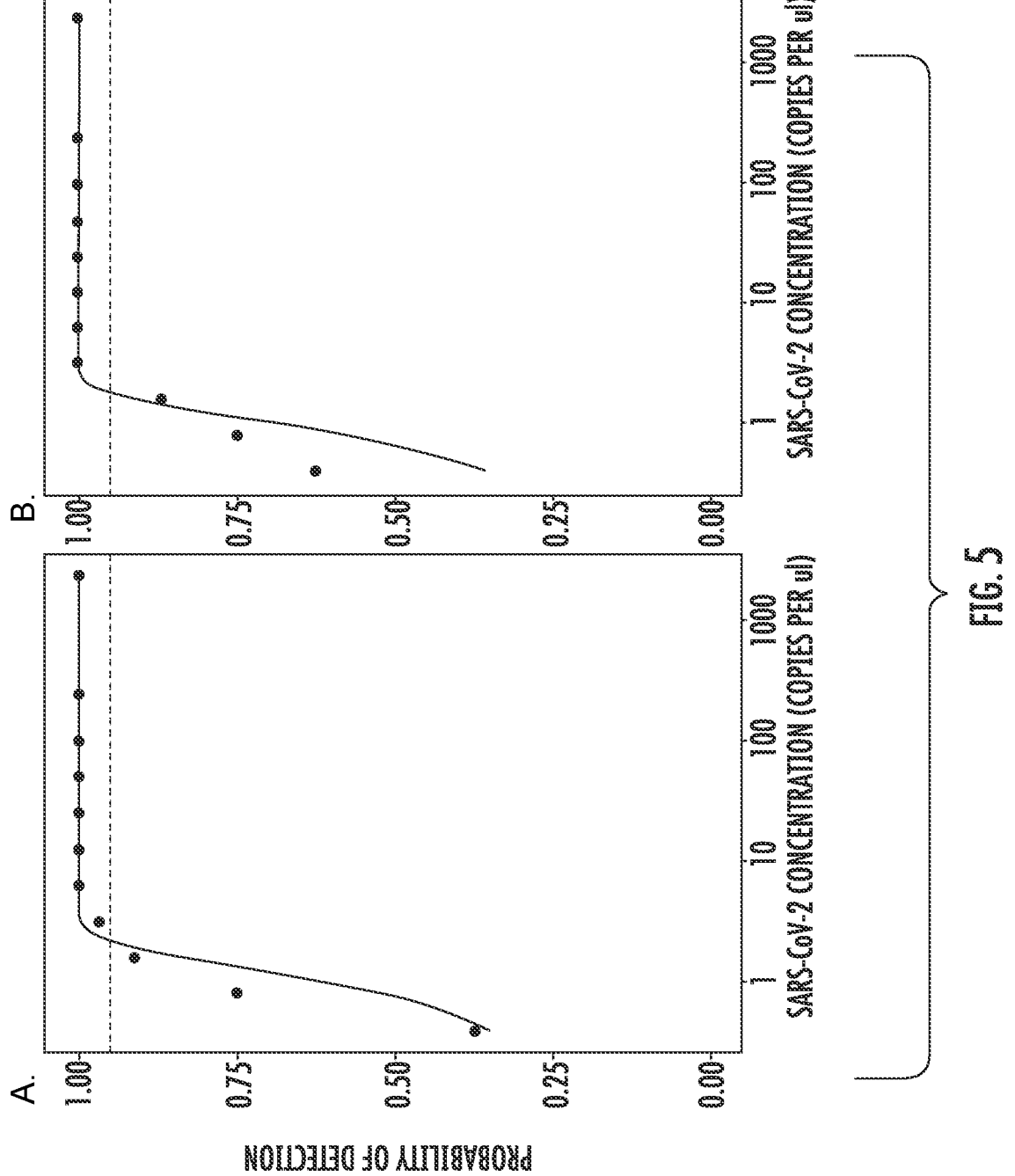
FIG. 5 depicts the probability of detection by SARS-CoV-2 concentration based on analytical sensitivity data. Dashed red line indicates a detection probability of 95% and the solid red line are predictions from a probit model.

Spiked remnant PBS samples were prepared by adding one-part quantified heat-inactivated SARS-CoV-2 (BEI Catalog No. NR-52286, Lot: 70034991) to nine-parts pooled negative remnant swab samples producing a 1:10 dilution of SARS-CoV-2 viruses. Final concentrations of SARS CoV-2 spiked samples were produced at 2,400, 240, 100, 50, 25, 12.5, 6.25, 3.13, 1.56, 0.78, and 0.39 genomes per μL. Samples were individually extracted and underwent rRT-PCR. The LoD was determined by aggregating the results of the individual extraction replicates across two days and identifying the lowest concentration at which at least 95% of the replicates (n>20) amplified. The lowest concentration at which 95% of replicates amplified was considered the LoD. Results showed that the LoD was 3.13 genomes per μL for TG-N2 (29/30 replicates; 97%) and TG-Spike4 (30/30 replicates; 100%) (TABLE 13). Additionally, a high degree of linearity was observed between $3.13-2.4 \times 10^3$ copies/μL for TG-N2 (R2=0.91), and TG-Spike4 (R2=0.86). Below the LoD, the probability of detection rapidly decreased for both the TG-N2 and the TG-Spike4 primer/probe sets (FIG. 5).

TABLE 13 depicts the aggregated data across dilutions for RNase P, TG-N2, and TG-Spike4. The LoD was determined to be the dilution with at least 95% extraction replicate detection (n>20 total replicates) across days. The LoD for TG-N2 and TG-Spike4 was determined to be 3.13 genomes per μL.

TABLE 13

| Data reported as (SD, % CV) [n detected/total]. | | | |
|---|---|---|---|
| Concentration (Genomes/μL) | RNase P | TG-N2 | TG-Spike4 |
| 2400 | 31.01 (0.79, 2.55%) [3/3] | 24.05 (0.56, 2.33%) [3/3] | 26.56 (0.59, 2.22%) [3/3] |
| 240 | 30.47 (0.42, 1.38%) [3/3] | 27.49 (0.21, 0.76%) [3/3] | 29.71 (0.15, 0.5%) [3/3] |
| 100 | 30.93 (0.14, 0.45%) [3/3] | 28.67 (0.08, 0.28%) [3/3] | 31.38 (0.27, 0.86%) [3/3] |
| 50 | 30.43 (1.07, 3.52%) [3/3] | 30.22 (0.71, 2.35%) [3/3] | 32.63 (0.44, 1.35%) [3/3] |
| 25 | 30.78 (0.84, 2.73%) [7/7] | 31.25 (0.43, 1.38%) [7/7] | 33.23 (0.35, 1.05%) [7/7] |
| 12.5 | 30.03 (0.4, 1.33%) [9/9] | 32.58 (0.74, 2.27%) [9/9] | 33.76 (0.19, 0.56%) [9/9] |
| 6.25 | 29.45 (1.4, 4.75%) [21/21] | 33.56 (1.27, 3.78%) [21/21] | 35.24 (0.79, 2.24%) [21/21] |
| 3.13 | 29.6 (0.83, 2.8%) [30/30] | 34.48 (1.16, 3.36%) [29/30] | 36.12 (0.87, 2.41%) [30/30] |
| 1.56 | 30.01 (0.71, 2.37%) [23/23] | 35.59 (0.82, 2.3%) [21/23] | 36.39 (0.99, 2.72%) [20/23] |
| 0.78 | 29.63 (0.89, 3%) [8/8] | 35.87 (1.27, 3.54%) [6/8] | 37.56 (0.37, 0.99%) [6/8] |
| 0.39 | 29.97 (1.47, 4.9%) [8/8] | 37.23 (0.62, 1.67%) [3/8] | 37.24 (1.16, 3.11%) [5/8] |
| NEC | ND (NA, NA %) [0/6] | ND (NA, NA %) [0/6] | ND (NA, NA %) [0/6] |
| NTC | ND (NA, NA %) [0/6] | ND (NA, NA %) [0/6] | ND (NA, NA %) [0/6] |
| PTC | 27.93 (0.16, 0.57%) [6/6] | 35.23 (0.65, 1.85%) [6/6] | 35.52 (0.73, 2.06%) [6/6] | iii. Precision

Quantified, heat-inactivated SARS-CoV-2 viruses were spiked into SARS-CoV-2 negative remnant swab material at four different dilutions (100, 6.25, 3.13, 1.56 genomes per µL) and frozen. Aliquots were extracted and tested per TGen TNCL protocols in duplicate across 17 batches. Results identified consistent Ct values across a total of 17 runs with similar standard deviations compared to the analytical sensitivity validation.

Figure 6:
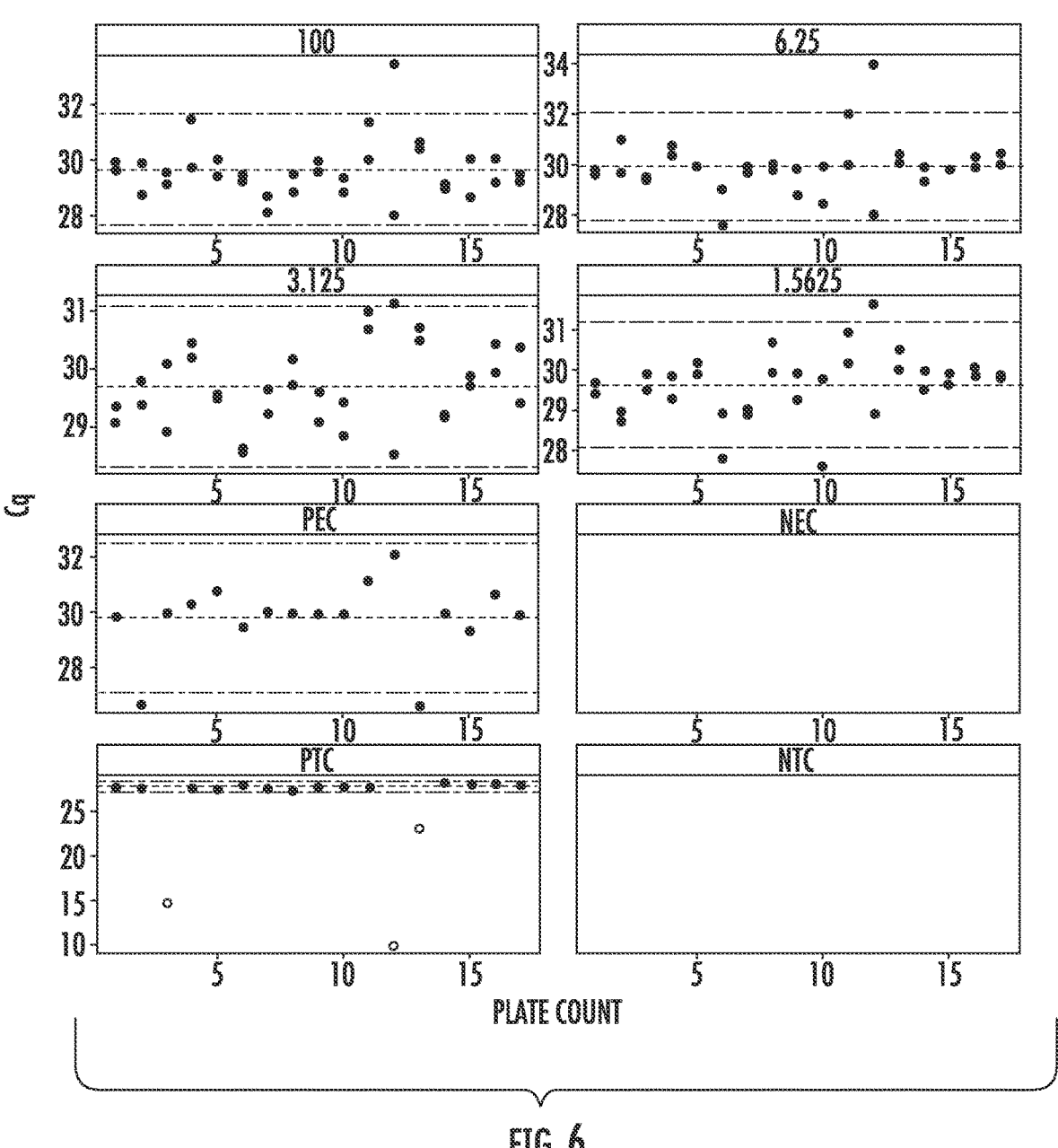
FIG. 6 depicts Cq values of spiked samples and controls across 10 batches for RNase P. Red lines indicate mean values and blue lines indicate +/−2 standard deviations. The outliers in the PTC panel (red points) were excluded from analyses due to evaporation.
Figure 7:
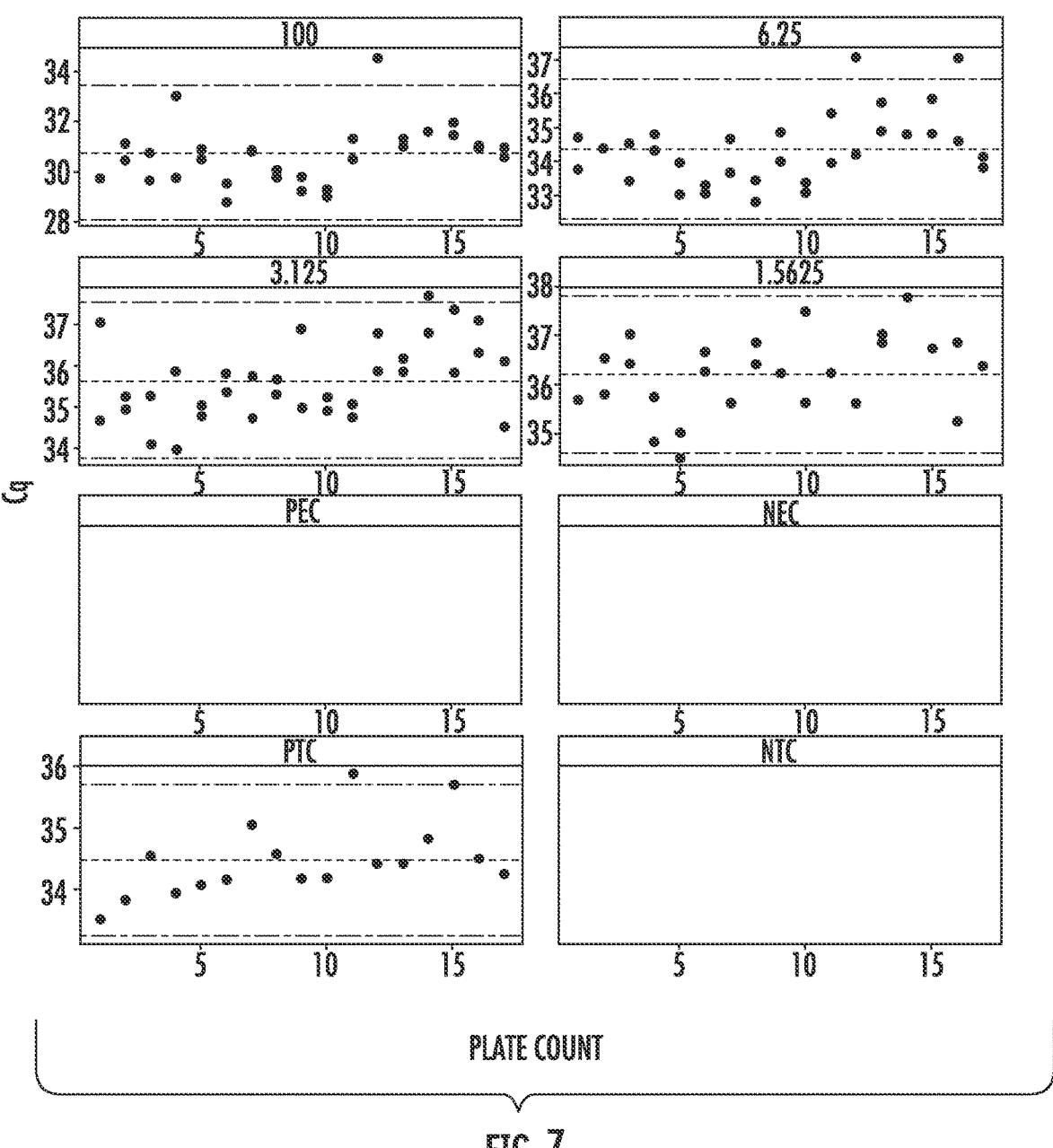
FIG. 7 depicts Cq values of spiked samples and controls across 10 batches for TG-N2. Red line indicates mean and blue lines indicate +/−2 standard deviations.
Figure 8:
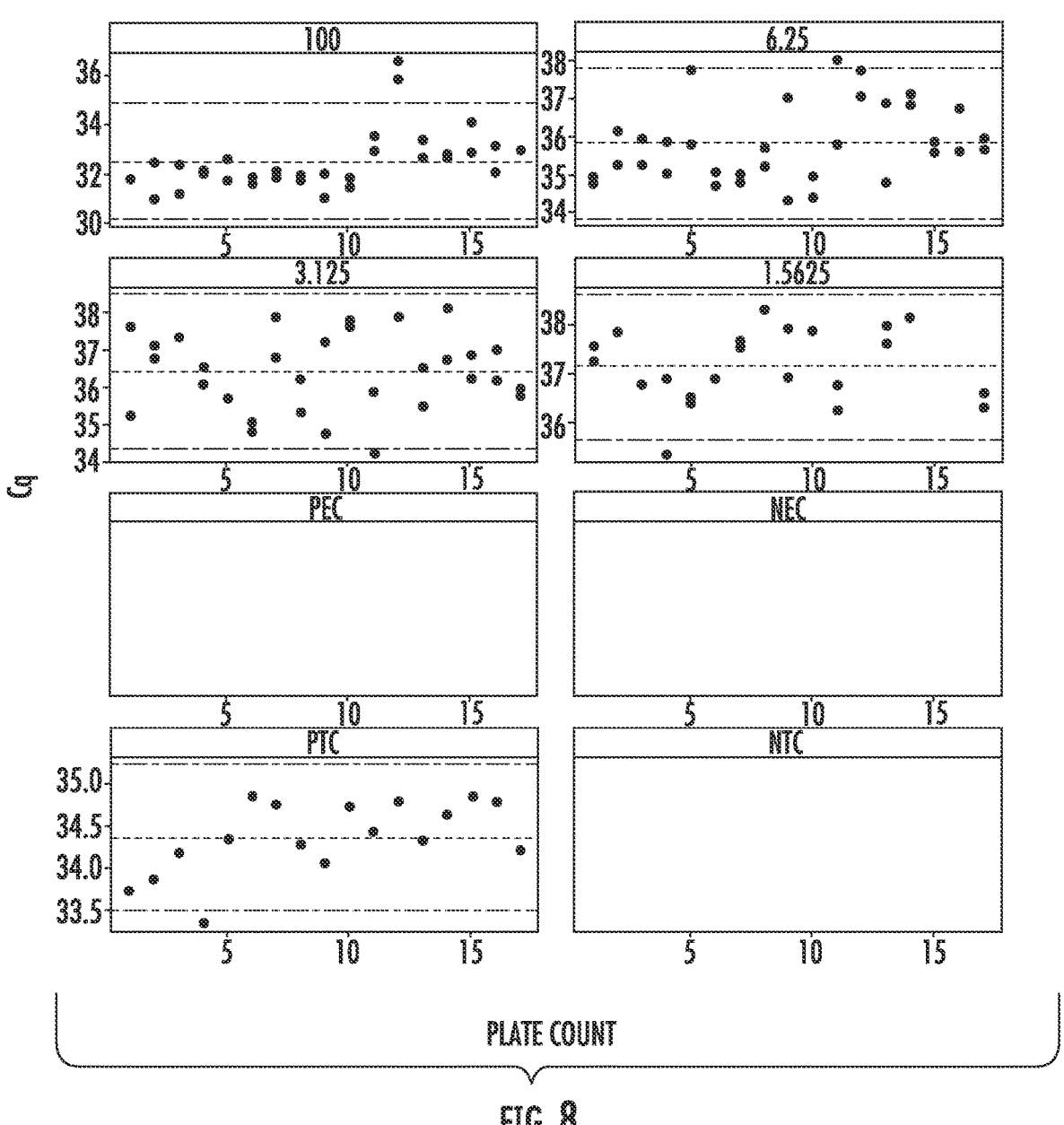
FIG. 8 depicts Cq values of contrived samples and controls across 10 batches for TG-Spike4. Red line indicates mean and blue lines indicate +/−2 standard deviations.

Spiked remnant PBS samples were prepared by adding one-part quantified heat-inactivated SARS-CoV-2 (BEI Catalog No. NR-52286, Lot: 70034991) to nine-parts pooled negative remnant swab samples producing a 1:10 dilution of SARS-CoV-2 viruses. Final concentrations of SARS CoV-2 spiked samples were produced at 100, 6.25, 3.13, and 1.56 genomes per µL. Samples were individually aliquoted and frozen. Samples were then thawed, extracted, and underwent rRT-PCR, with individually-made mastermix to simulate day to day variation in reagents. Results showed similar results to analytical sensitivity, with a slight loss in sensitivity demonstrated by a slight increase (~0.5-1) in Cq values and slight loss of reproducibility at the LoD (90% for TG-Spike4). This loss in sensitivity is consistent with loss due to a freeze thaw cycle. The freeze thaw cycle was incorporated to allow precision samples to be periodically run across the next few months for continued precision monitoring (FIGS. 6-8).

TABLE 14 depicts the results of a precision study for four different dilutions and associated controls.

TABLE 14

Data reported as mean (SD, % CV) [n detected/total].

| Sample Conc. (Genomes per µL) | CDC-RP | TG-N2 | TG-S4 |
|---|---|---|---|
| 100 | 29.72 (1, 3.36%) [34/34] | 30.77 (1.33, 4.32%) [34/34] | 32.45 (1.12, 3.45%) [34/34] |
| 6.25 | 29.94 (1.07, 3.57%) [34/34] | 34.38 (1.05, 3.05%) [33/34] | 35.82 (1, 2.79%) [34/34] |
| 3.125 | 29.7 (0.68, 2.29%) [34/34] | 35.65 (0.95, 2.66%) [34/34] | 36.44 (1.06, 2.91%) [31/34] |
| 1.5625 | 29.64 (0.78, 2.63%) [34/34] | 36.21 (0.81, 2.24%) [26/34] | 37.14 (0.73, 1.97%) [23/34] |
| NEC | ND (NA, NA %) [0/17] | ND (NA, NA %) [0/17] | ND (NA, NA %) [0/17] |
| NTC | ND (NA, NA %) [0/17] | ND (NA, NA %) [0/17] | ND (NA, NA %) [0/17] |
| PEC | 29.8 (1.36, 4.56%) [17/17] | ND (NA, NA %) [0/17] | ND (NA, NA %) [0/17] |
| PTC | 27.74 (0.24, 0.87%) [14/14]* | 34.48 (0.61, 1.77%) [17/17] | 34.37 (0.44, 1.28%) [17/17] |

*Three samples were excluded due to evaporation.

iv. Accuracy

A total of 251 remnant TNCL clinical samples (122 positive, 117 negative, and 12 inconclusive) were tested with the SARS-CoV-2 Direct Assay. Overall, results showed 90.4% concordance between the TNCL SARS-CoV-2 Direct LDT and TNCL SARS-CoV-2 rRT-PCR LDT. The loss of sensitivity was observed near and beyond the limit of detection of the TNCL SARS-CoV-2 Direct Assay.

Figure 9:
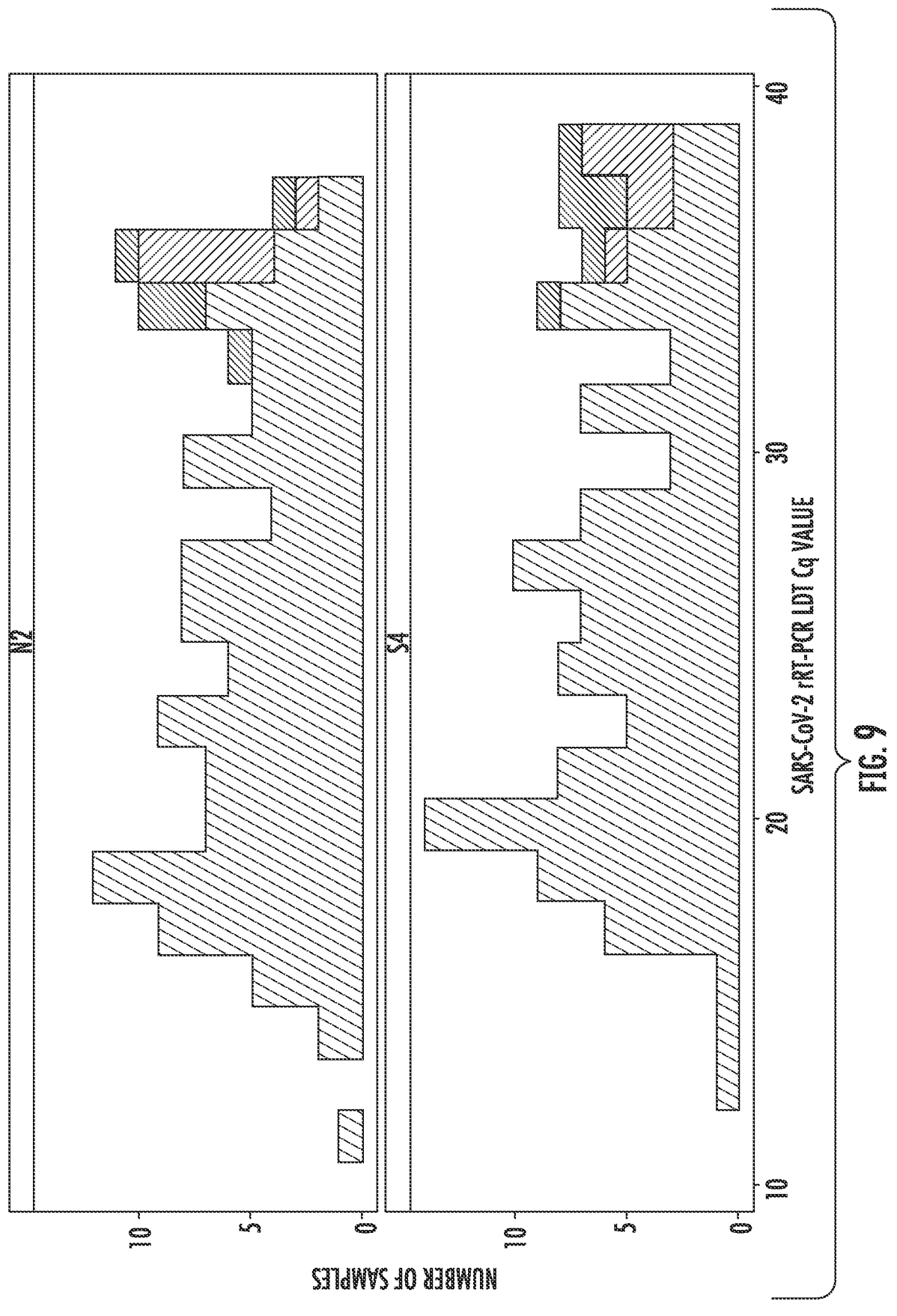
FIG. 9 depicts a comparison of positive TNCL SARS-CoV-2 rRT-PCR Cq results (numerical) to TNCL SARS-CoV-2 Direct result (positive, negative, inconclusive). Purple indicates SARS-CoV-2 Direct positive results, blue indicates SARS-CoV-2 Direct inconclusive results, and red indicates negative SARS-CoV-2 Direct results.
Figure 10:
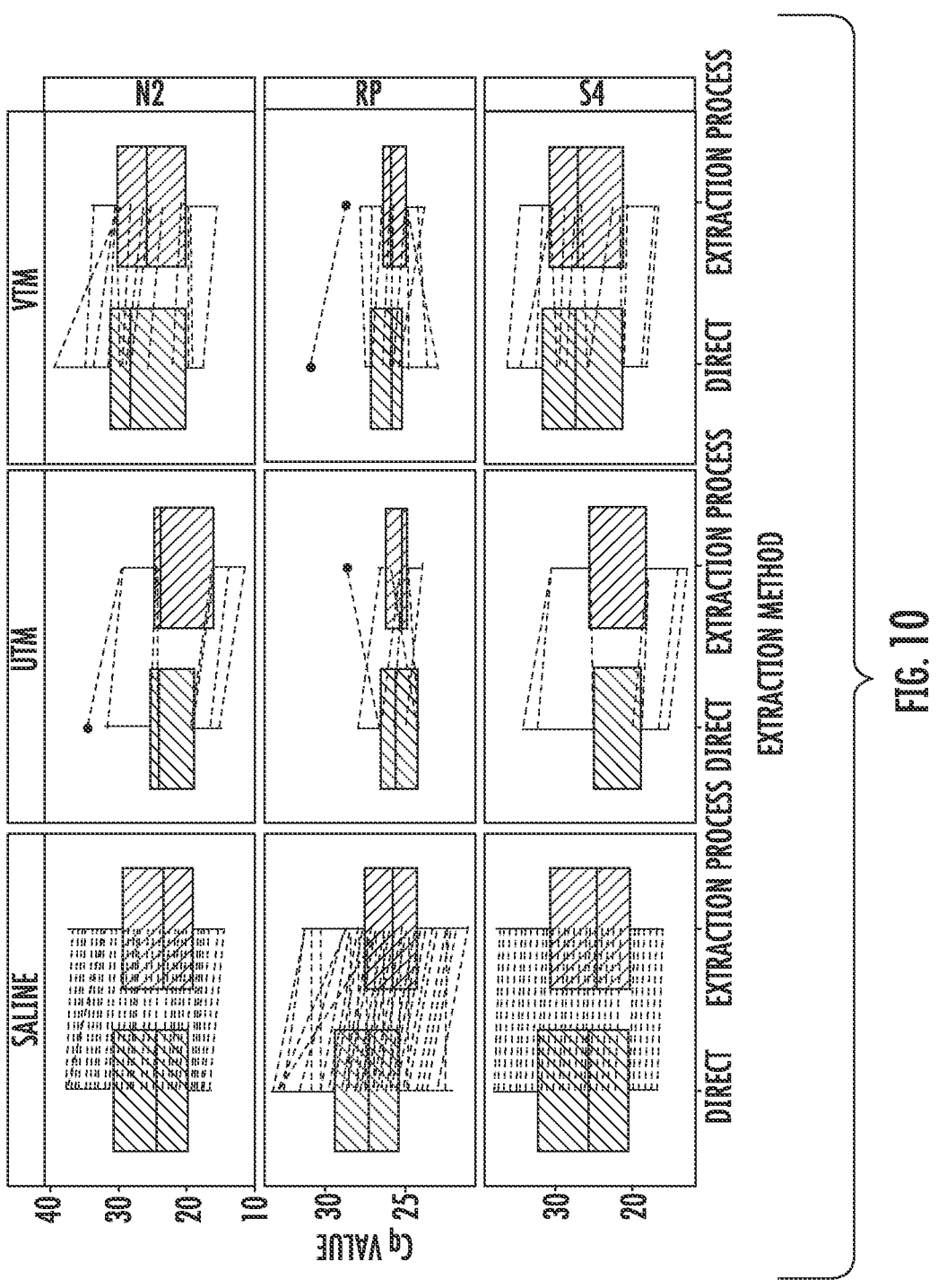
FIG. 10 depicts a comparison of Cq values for positive NP samples run on the SARS-CoV-2 Direct Assay and the traditional TNCL SARS-CoV-2 rRT-PCR assay.

TNCL SARS-CoV-2 Direct procedures were used to test remnant NP swab material that was previously tested by the TNCL SARS-CoV-2 rRT-PCR LDT. If samples were fresh, TNCL results were directly used; if samples went through a freeze thaw, TNCL SARS-CoV-2 rRT-PCR LDT values were generated by retesting. A total of 251 remnant TNCL clinical samples (122 positive, 117 negative, and 12 inconclusive) were tested for this clinical evaluation. Samples were tested in saline (n=219), universal transport media (UTM; n=10), and viral transport media (VTM; n=22). Across all media types, results showed overall agreement of 90.4% between TNCL SARS-CoV-2 Direct LDT and TNCL SARS-CoV-2 rRT-PCR LDT (TABLES 15 and 16). Sensitivity of positive results was 89.3% and 94.0% when excluding inconclusive calls (TABLES 16). Comparing results of the SARS-CoV-2 Direct Assay to the Cq values of the TNCL SARS-CoV-2 rRT-PCR, discordant samples were seen at higher Cq values. These samples were near the limit of detection of both assays; thus, discordance in these samples could be due to stochasticity of sampling at these low concentrations or a slight loss of sensitivity due to not running samples through the Zymo extraction process (FIG. 9). With the Direct protocols, a minimal, but statistically significant, increase in Cq was observed across all assays (TG-N2: delta=1.18 Cq, p-value=$1.15 \times 10^{-9}$, TG-S4: delta=0.68 Cq, p-value=$3.4 \times 10^{-5}$, RNase P: delta=1.24 Cq, p-value=$1.07 \times 10^{-12}$; FIG. 10). Therefore, with the SARS-CoV-2 direct test, a slight loss of sensitivity is expected; however, this loss of sensitivity is only expected to be near or beyond the LoD of both the TNCL SARS-CoV-2 Direct LDT and TNCL SARS-CoV-2 rRT-PCR LDT.

TABLE 15

Confusion matrices for clinical evaluation across media types of TNCL SARS-CoV-2 Direct LDT.

|  |  |  | TNCL SARS-CoV-2 rRT-PCR LDT | | |
|  |  |  | Positive | Negative | Inconclusive |
| --- | --- | --- | --- | --- | --- |
| TNCL SARS-CoV-2 Direct LDT | All Media Types | Positive | 109 | 0 | 0 |
|  |  | Negative | 7 | 117 | 11 |
|  |  | Inconclusive | 6 | 0 | 1 |
|  | Saline | Positive | 86 | 0 | 0 |
|  |  | Negative | 5 | 112 | 10 |
|  |  | Inconclusive | 6 | 0 | 0 |
|  | UTM | Positive | 9 | 0 | 0 |
|  |  | Negative | 1 | 0 | 0 |
|  |  | Inconclusive | 0 | 0 | 0 |

TABLE 15-continued

Confusion matrices for clinical evaluation across media types of TNCL SARS-CoV-2 Direct LDT.

|  |  | TNCL SARS-CoV-2 rRT-PCR LDT | | |
|  |  | Positive | Negative | Inconclusive |
| --- | --- | --- | --- | --- |
| VTM | Positive | 14 | 0 | 0 |
|  | Negative | 1 | 5 | 1 |
|  | Inconclusive | 0 | 0 | 1 |

TABLE 16

Accuracy metrics for clinical evaluation across all media types.

| Accuracy Metrics | Positive | Negative | Inconclusive |
| --- | --- | --- | --- |
| Sensitivity | 0.8934 | 1.0000 | 0.0833 |
| Specificity | 1.0000 | 0.8657 | 0.9749 |
| Pos. Pred. Value | 1.0000 | 0.8667 | 0.1429 |
| Neg Pred. Value | 0.9085 | 1.0000 | 0.9549 |
| Precision | 1.0000 | 0.8667 | 0.1429 |
| Recall | 0.8934 | 1.0000 | 0.0833 |
| F1 | 0.9437 | 0.9286 | 0.1053 |
| Prevalence | 0.4861 | 0.4661 | 0.0478 |
| Detection Rate | 0.4343 | 0.4661 | 0.0040 |
| Detection Prevalence | 0.4343 | 0.5378 | 0.0279 |
| Balanced Accuracy | 0.9467 | 0.9328 | 0.5291 | f. Reportable Range of Test Results for the Test System

A high degree of linearity was observed between 3.13-$2.4 \times 10^3$ copies/uL for TG-N2, R2=0.91, and TG-Spike4, R2=0.86. Below the LoD, the probability of detection rapidly decreased for both the TG-N2 and the TG-Spike4 primer/probe sets.

g. Additional Validation for Alternative Specimens and Mastermix

Heat-inactivated SARS-CoV-2 was serially diluted into remnant clinical PBS. Several replicates of 50 μL of spiked samples were processed with the Proteinase K extraction process using Proteinase K from 2 different manufactures (Qiagen, AmericanBio), and both TG RT-qPCR and CDC-RP targets were tested per TGen TNCL protocols.

Spiked remnant PBS samples were prepared by adding one-part quantified heat-inactivated SARS-CoV-2 (BEI Catalog No. NR-52286, Lot: 70034991) to nine-parts pooled negative remnant swab samples producing a 1:10 dilution of SARS-CoV-2 viruses. Final concentrations of SARS CoV-2 spiked samples were produced at 240, 100, 50, 25, 12.5, 6.25, 3.13, 1.56, 0.78, 0.39 genomes per μL. Individual samples were processed via the Proteinase K extraction, once with Qiagen (Lot: 157033314) and once with AmericanBio (Lot: 18489800). The results between Qiagen and AmericanBio Proteinase K are comparable with slight variation in Cq values; however, no statistical significance was observed (TG-N2: delta=−0.37 Cq, p-value=0.1788 Cq; TG-S4: delta=0.54, p-value=0.015; RNase P: delta=1.06 Cq, p-value=0.1352; TABLES 17 and 18).

TABLE 17

Results of Proteinase K study for 10 different dilutions and associated controls using Qiagen manufactured Proteinase K. Mean (SD, % CV) [n detected/total].

| Final Sample Concentration (genomes/μL) | RNase P | TG-N2 | TG-Spike4 |
| --- | --- | --- | --- |
| 240 | NaN (NA, NA %) [0/2]* | 28.21 (0.08, 0.28%) [2/2] | 28.62 (0.29, 1.01%) [2/2] |
| 100 | NaN (NA, NA %) [0/2]* | 29.92 (0.06, 0.2%) [2/2] | 29.89 (0.13, 0.43%) [2/2] |

US 12,674,200 B2

37

38

TABLE 17-continued

Results of Proteinase K study for 10 different dilutions and associated controls
using Qiagen manufactured Proteinase K. Mean (SD, % CV) [n detected/total].

| Final Sample Concentration (genomes/µL) | RNase P | TG-N2 | TG-Spike4 |
|---|---|---|---|
| 50 | 27.94 (0.03, 0.11%) [2/2] | 28.32 (0.09, 0.32%) [2/2] | 30.36 (0.89, 2.93%) [2/2] |
| 25 | 27.77 (0.63, 2.27%) [2/2] | 30.17 (0.17, 0.56%) [2/2] | 32.85 (0.13, 0.40%) [2/2] |
| 12.5 | 29.13 (0.14, 0.48%) [2/2] | 33.65 (0.08, 0.24%) [2/2] | 33.72 (0.39, 1.16%) [2/2] |
| 6.25 | 29.86 (0.01, 0.03%) [2/2] | 35.24 (0.12, 0.34%) [2/2] | 35.68 (1.02, 2.86%) [2/2] |
| 3.13 | 29.61 (0.15, 0.51%) [4/4] | 36.02 (0.96, 2.67%) [4/4] | 36.11 (0.37, 1.02%) [4/4] |
| 1.56 | 29.44 (0.11, 0.37%) [2/2] | 37.25 (NA, NA %) [1/2] | 36.56 (0.51, 1.39%) [2/2] |
| 0.78 | 28.17 (2.55, 9.05%) [2/2] | 38.05 (NA, NA %) [1/2] | NaN (NA, NA %) [0/2] |
| 0.39 | 27.94 (0.03, 0.11%) [2/2] | NaN (NA, NA %) [0/2] | 38.26 (NA, NA %) [1/2] |
| NEC | NaN (NA, NA %) [0/1] | NaN (NA, NA %) [0/1] | NaN (NA, NA %) [0/1] |
| NTC | NaN (NA, NA %) [0/1] | NaN (NA, NA %) [0/1] | NaN (NA, NA %) [0/1] |
| PEC | 29.57 (NA, NA %) [1/1] | NaN (NA, NA %) [0/1] | NaN (NA, NA %) [0/1] |
| PTC | 27.46 (NA, NA %) [1/1] | 34.56 (NA, NA %) [1/1] | 35.71 (NA, NA %) [0/1] |

*Technician error; no CDC-RP mastermix was added to the wells containing sample for HI1 and HI2.

TABLE 18

Results of Proteinase K study for 10 different dilutions and associated controls
using AmericanBio-manufactured Proteinase K. Mean (SD, % CV) [n detected/total].

| Final Sample Concentration (genomes/µL) | RNase P | TG-N2 | TG-Spike4 |
|---|---|---|---|
| 240 | 27.94 (0.05, 0.18%) [2/2] | 28.17 (0.21, 0.75%) [2/2] | 28.45 (0.42, 1.48%) [2/2] |
| 100 | 28.06 (0.05, 0.18%) [2/2] | 29.95 (0.19, 0.63%) [2/2] | 29.66 (0.24, 0.81%) [2/2] |
| 50 | 27.68 (0.24, 0.87%) [2/2] | 30.47 (0.41, 0.19%) [2/2] | 30.85 (0.09, 0.29%) [2/2] |
| 25 | 27.63 (0.34, 1.23%) [2/2] | 32.04 (0.07, 0.22%) [2/2] | 32.03 (0.12, 0.37%) [2/2] |
| 12.5 | 29.37 (0.36, 1.23%) [2/2] | 33.71 (0.74, 2.2%) [2/2] | 33.34 (0.60, 1.8%) [2/2] |
| 6.25 | 29.35 (0.15, 0.51%) [2/2] | 34.76 (0.92, 2.65%) [2/2] | 34.14 (0.53, 1.55%) [2/2] |
| 3.13 | 28.33 (1.54, 5.44%) [4/4] | 36.95 (0.81, 2.19%) [3/4] | 35.67 (0.94, 2.64%) [4/4] |
| 1.56 | 29.26 (0.43, 1.47%) [2/2] | 36.52 (1.07, 2.93%) [2/2] | 35.99 (0.00, 0.00%) [2/2] |
| 0.78 | 28.43 (0.78, 2.74%) [2/2] | 36.30 (0.47, 1.29%) [2/2] | 36.25 (NA, NA %) [1/2] |
| 0.39 | 28.86 (0.21, 0.87%) [2/2] | 37.14 (0.07, 0.19%) [2/2] | 36.68 (1.03, 2.81%) [2/2] |
| NEC | NaN (NA, NA %) [0/1] | NaN (NA, NA %) [0/1] | NaN (NA, NA %) [0/1] |
| NTC | NaN (NA, NA %) [0/1] | NaN (NA, NA %) [0/1] | NaN (NA, NA %) [0/1] |
| PEC | 28.84 (NA, NA %) [1/1] | NaN (NA, NA %) [0/1] | NaN (NA, NA %) [0/1] |
| PTC | 14.09 (NA, NA %) [1/1] | 34.63 (NA, NA %) [1/1] | 34.06 (NA, NA %) [1/1] |

3. Targeted Amplicon Sequencing

Amplicon-based sequencing can be used in the identification of one or more markers for the detection of SARS-CoV-2. Some embodiments of the invention include systems and methods of preparing samples for one or more downstream processes that can be used for assessing one or more markers for the detection of SARS-CoV-2.

For a targeted amplicon sequencing method, amplicon library preparation may be performed using the universal tail indexing strategy, i.e., using primers having universal tails. A universal indexing sequencing strategy can be used to amplify multiple genomic regions (e.g., markers, as described below) from a DNA sample simultaneously in a single reaction for the sequencing of one or more amplicons. Some embodiments of the invention comprise multiple steps and/or processes that are carried out to execute the universal tail indexing strategy to prepare amplicons for sequencing.

TABLE 19 shows primers for an amplicon sequencing assay targeting the N protein gene and the spike protein gene of SARS-CoV-2. In various embodiments, the SARS-CoV-2 amplicon sequencing assay comprises four amplicon sequencing assay primers (SEQ ID NOS: 9-12), and may further include indexing primers and sequencing primers.

gene-specific sequence and a universal tail sequence, the universal tail sequences are underlined in TABLE 19. The forward primers have a first universal tail sequence, and the reverse primers have a second universal tail sequence, with the second universal tail sequence being different than the first universal tail sequence. For example, the forward primers (SEQ ID NOS: 9 and 11) include a first universal tail sequence (SEQ ID NO: 13), and the reverse primers (SEQ ID NOS: 10 and 12) include a second universal tail sequence (SEQ ID NO: 14). The amplification of the target results in the production of amplicons that comprise the first and second universal tail sequences integrated therein. After production of the amplicons during the multiplex PCR assay, the resulting amplicons can be further processed an indexing extension step to provide sequencing-ready amplicons.

Second PCR: The indexing extension PCR adds a specific index sequence to the amplicons using the universal tail sequences on either end of the amplicon. Stated differently, the amplicons are extended using platform-specific primers that recognize at least one of UT1 and UT2 for adding the indexes to each amplicon. The index is unique for each sample, such that the indexing primer includes a sample-specific index sequence and a common universal tail

TABLE 19

| | Assay Component | Name | Sequence | SEQ ID NO: |
|---|---|---|---|---|
| N protein gene: TG-N2 assay | forward primer | TG-N2_F (AmpSeq) | ACCCAACTGAATGGAGCTTCAG CGTTCTTCGGAATGTC | 9 |
| | reverse primer | TG-N2_R (AmpSeq) | ACGCACTTGACTTGTCTTCTGG CACCTGTGTAGGTCAAC | 10 |
| S protein gene: TG-spike4 assay | forward primer | TG-spike4_F (AmpSeq) | ACCCAACTGAATGGAGCCCAGT TGCTGTAGTTGTCTCAAG | 11 |
| | reverse primer | TG-spike4_R (AmpSeq) | ACGCACTTGACTTGTCTTCCTG GCTCAGAGTCGTCTTCA | 12 |
| Universal Tails | | UT1 | ACCCAACTGAATGGAGC | 13 |
| | | UT2 | ACGCACTTGACTTGTCTTC | 14 |

An amplicon sequencing assay may include the TG-N2 (AmpSeq) primers, SEQ ID NOS: 9 and 10, and may further include the TG-spike4 (AmpSeq) primers, SEQ ID NOS: 11 and 12.

In TABLE 19, the universal tails, which are added to the primers for amplicon sequencing, are underlined. Universal tail sequences are ACCCAACTGAATGGAGC (SEQ ID NO: 13) for forward read and ACGCACTTGACTTGTCTTC (SEQ ID NO: 14) for reverse read. The universal tail sequences (underlined) precede the assay-specific primer sequence (not underlined), for example, in SEQ ID NOS: 9, 10, 11 and 12.

The amplicon sequencing method may include creating a series of oligonucleotides designed to provide multiplexed amplification of one or more markers to produce the desired amplicons. After production of the amplicons (e.g., via PCR amplification), which may include the universal tail sequences, the resulting amplicons can be further processed to provide sequencing-ready amplicons. The method may further include performing downstream sequencing on the sequencing-ready amplicons.

The amplicon library preparation comprises two PCR steps, a gene-specific multiplex PCR and an index extension PCR.

First PCR: In gene-specific multiplex PCR reactions, the target amplicons are synthesized with a universal tail sequence added to the amplicons. Each primer includes a complement sequence. Thus, the number of different indexing primers used in the second PCR depends on the number of unique samples being processed in the same PCR. Each indexing primer comprises a complementary sequence that recognizes at least one of the first universal tail sequence and the second universal tail sequence that has been previously integrated within the amplicons. At the end of the index extension PCR there is a sequencer-ready amplicon library. By adding sample specific index sequences to the amplicons, pools of several samples are made ready for sequencing. The samples can be pooled for sequencing using a desired platform during a single sequencing run and distinguished based on the index sequence during analysis of the data. The inclusion of the universal tail sequences (SEQ ID NOS: 13 and 14) on the index and common primers may coincide with the use of genomic and index read primers in the mixture of sequencing primer reagents. After sequencing, the resulting data can be de-multiplexed and the sequence files can be aligned to a reference sequence (e.g., a wild type sequence and/or other alleles for each of the respective markers) for subsequent sequence analyses. As a result, the aligned sequences can be analyzed for the presence or absence of markers, variant signatures associated with the markers, differential marker presence in the sample, which includes the capability of analyzing gene expression, and an estimate of allele frequencies of various alleles of the markers in the pooled samples.

For example, the second PCR, using the universal tail-specific primers, adds Illumina's sample-specific index and sequencing adapters. Samples may then be pooled in equimolar concentration for sequencing. The amplicons may be sequenced by next-generation sequencing using a desired platform, such as the Illumina® MiSeq platform. Methods of sequencing include but need not be limited to any form of DNA sequencing including Sanger, next-generation sequencing, pyrosequencing, SOLiD sequencing, massively parallel sequencing, pooled, and barcoded DNA sequencing or any other sequencing method now known or yet to be disclosed. The number or quantity of sequencing reads for a particular gene or marker can be counted for each sample. In some aspects, the amplicons resulting from the multiplex PCR reaction can be sequenced, and the resulting sequences can be aligned to a reference sequence. As a result, differential numbers of sequence reads generated by the sequencing process (i.e., when aligned to the amplicon reference sequences), can provide data regarding the different copy numbers in the original RNA sample. The sequencing data or sequencing reads can be analyzed for identification and detection of SARS-CoV-2.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. Two pairs of oligonucleotides for amplifying SARS-CoV-2 N and S proteins, each oligonucleotide having a 5' terminus and a 3' terminus, wherein the nucleotide sequence of each oligonucleotide consists of 40 or less nucleotides; and the nucleotide sequence of each oligonucleotide comprises:

a nucleotide sequence that binds to a viral genome, said nucleotide sequence for the first primer pair consisting of the nucleotide sequence of: SEQ ID NO: 1 and SEQ ID NO: 2, and said nucleotide sequence for the second primer pair consisting of the nucleotide sequence of: SEQ ID NO:5 and SEQ ID NO:6; and a universal tail sequence, wherein the universal tail sequence is 5' to the nucleotide sequence that binds to a viral genome, does not bind to the viral genome, and is capable of acting as a template for amplification with a primer complementary to the universal tail sequence.

2. A method of detecting the presences of severe acute respiratory syndrome coronavirus 2 (SARS-CoV-2) polynucleotides in a biological sample in vitro, comprising:

(a) mixing the biological sample in vitro with two primer pairs, each capable of amplifying a SARS-CoV-2 amplicon product, if the SARS-CoV-2 polynucleotide is present in the biological sample, wherein each primer of each primer pair consists of 40 or less nucleotides and the nucleotide sequence of each primer comprises:

a nucleotide sequence capable of detecting SARS-CoV-2, wherein the first primer pair amplifies a nucleocapsid protein amplicon product of SARS-CoV-2 and consists of the nucleotide sequence of: SEQ ID NO: 1 and SEQ ID NO:2, and the second primer pair amplifies a spike protein gene amplicon product of SARS-CoV-2 and consists of the nucleotide sequence of: SEQ ID NO:5 and SEQ ID NO:6; and a universal tail sequence, wherein the universal tail sequence is 5' to the nucleotide sequence, does not bind to the SARS-CoV-2 genome, and is capable of acting as a template for amplification with a primer complementary to the universal tail sequence;

(b) amplifying the SARS-CoV-2 amplicon products;

(c) sequencing the amplicon products; and (d) detecting whether SARS-CoV-2 polynucleotides are present in the biological sample by analyzing the sequencing reads.

3. The method of claim 2, wherein the amplicon product has a nucleotide sequence that consists essentially of SEQ ID NO:4 or SEQ ID NO:8.

4. The method of claim 2, wherein the biological sample comprises a nasopharyngeal swab sample or sputum.

5. The method of claim 2, wherein:

the sequence of one primer of the first primer pair consists of:

SEQ ID NO:9;

the sequence of the other primer of the first primer pair consists of:

SEQ ID NO:10;

the sequence of one primer of the second primer pair consists of:

SEQ ID NO:11; and the sequence of the other primer of the second primer pair consists of:

SEQ ID NO:12.

* * * * *

```
                          SEQUENCE LISTING

Sequence total quantity: 14
SEQ ID NO: 1            moltype = DNA   length = 21
FEATURE                Location/Qualifiers
misc_feature           1..21
                       note = Primer
source                 1..21
                       mol_type = other DNA
                       organism = synthetic construct
SEQUENCE: 1
ttcagcgttc ttcggaatgt c                                              21

SEQ ID NO: 2            moltype = DNA   length = 20
FEATURE                Location/Qualifiers
misc_feature           1..20
                       note = Primer
source                 1..20
                       mol_type = other DNA
                       organism = synthetic construct
SEQUENCE: 2
tggcacctgt gtaggtcaac                                                20

SEQ ID NO: 3            moltype = DNA   length = 23
FEATURE                Location/Qualifiers
misc_feature           1..23
                       note = Probe
source                 1..23
                       mol_type = other DNA
                       organism = synthetic construct
SEQUENCE: 3
cgcattggca tggaagtcac acc                                            23

SEQ ID NO: 4            moltype = DNA   length = 77
FEATURE                Location/Qualifiers
source                 1..77
                       mol_type = genomic DNA
                       organism = Severe acute respiratory syndrome-related
                        coronavirus
SEQUENCE: 4
ttcagcgttc ttcggaatgt cgcgcattgg catggaagtc acaccttcgg gaacgtggtt   60
gacctacaca ggtgcca                                                   77

SEQ ID NO: 5            moltype = DNA   length = 23
FEATURE                Location/Qualifiers
misc_feature           1..23
                       note = Primer
source                 1..23
                       mol_type = other DNA
                       organism = synthetic construct
SEQUENCE: 5
ccagttgctg tagttgtctc aag                                            23

SEQ ID NO: 6            moltype = DNA   length = 20
FEATURE                Location/Qualifiers
misc_feature           1..20
                       note = Primer
source                 1..20
                       mol_type = other DNA
```

```
                          organism = synthetic construct
SEQUENCE: 6
ctggctcaga gtcgtcttca                                                20

SEQ ID NO: 7             moltype = DNA   length = 24
FEATURE                  Location/Qualifiers
misc_feature             1..24
                         note = Probe
source                   1..24
                         mol_type = other DNA
                         organism = synthetic construct
SEQUENCE: 7
tgttgttctt gtggatcctg ctgc                                           24

SEQ ID NO: 8             moltype = DNA   length = 78
FEATURE                  Location/Qualifiers
source                   1..78
                         mol_type = genomic DNA
                         organism = Severe acute respiratory syndrome-related
                          coronavirus
SEQUENCE: 8
ccagttgctg tagttgtctc aagggctgtt gttcttgtgg atcctgctgc aaatttgatg   60
aagacgactc tgagccag                                                  78

SEQ ID NO: 9             moltype = DNA   length = 38
FEATURE                  Location/Qualifiers
misc_feature             1..38
                         note = Primer
source                   1..38
                         mol_type = other DNA
                         organism = synthetic construct
SEQUENCE: 9
acccaactga atggagcttc agcgttcttc ggaatgtc                            38

SEQ ID NO: 10            moltype = DNA   length = 39
FEATURE                  Location/Qualifiers
misc_feature             1..39
                         note = Primer
source                   1..39
                         mol_type = other DNA
                         organism = synthetic construct
SEQUENCE: 10
acgcacttga cttgtcttct ggcacctgtg taggtcaac                           39

SEQ ID NO: 11            moltype = DNA   length = 40
FEATURE                  Location/Qualifiers
misc_feature             1..40
                         note = Primer
source                   1..40
                         mol_type = other DNA
                         organism = synthetic construct
SEQUENCE: 11
acccaactga atggagccca gttgctgtag ttgtctcaag                          40

SEQ ID NO: 12            moltype = DNA   length = 39
FEATURE                  Location/Qualifiers
misc_feature             1..39
                         note = Primer
source                   1..39
                         mol_type = other DNA
                         organism = synthetic construct
SEQUENCE: 12
acgcacttga cttgtcttcc tggctcagag tcgtcttca                           39

SEQ ID NO: 13            moltype = DNA   length = 17
FEATURE                  Location/Qualifiers
misc_feature             1..17
                         note = Universal Tail
source                   1..17
                         mol_type = other DNA
                         organism = synthetic construct
SEQUENCE: 13
acccaactga atggagc                                                   17

SEQ ID NO: 14            moltype = DNA   length = 19
FEATURE                  Location/Qualifiers
misc_feature             1..19
                         note = Universal Tail
source                   1..19
```

-continued

```
                        mol_type = other DNA
                        organism = synthetic construct
SEQUENCE: 14
acgcacttga cttgtcttc                                                    19
```